United States Patent
Gooch et al.

(10) Patent No.: US 6,392,232 B1
(45) Date of Patent: *May 21, 2002

(54) HIGH FILL FACTOR BOLOMETER ARRAY

(75) Inventors: Roland W. Gooch, Dallas; Mark V. Wadsworth, Richardson, both of TX (US)

(73) Assignee: Pharmarcopeia, Inc., Cranbury, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/690,274

(22) Filed: Jul. 19, 1996

Related U.S. Application Data

(60) Provisional application No. 60/001,331, filed on Jul. 21, 1995.

(51) Int. Cl.[7] .................................................. G01J 5/10
(52) U.S. Cl. .................................... 250/332; 250/338.4
(58) Field of Search ............................... 250/332, 338.4

(56) References Cited

U.S. PATENT DOCUMENTS

| | | | |
|---|---|---|---|
| 5,010,251 A | | 4/1991 | Grinberg et al. |
| 5,017,784 A | * | 5/1991 | Sher et al. ................ 250/338.1 |
| 5,300,915 A | * | 4/1994 | Higashi et al. ........... 338/22 R |
| 5,399,897 A | | 3/1995 | Cunningham et al. |
| 5,602,043 A | * | 2/1997 | Beratan et al. ................ 438/54 |

FOREIGN PATENT DOCUMENTS

| | | | |
|---|---|---|---|
| EP | 0354369 | * 2/1990 | .............. 250/338.4 |
| EP | 0 354 369 A2 | 2/1990 | |
| EP | 0 534 768 A1 | 3/1993 | |

OTHER PUBLICATIONS

R. A. Wood, "High–Performance Infrared Thermal Imaging with Monolithic Silicon Focal Planes Operating at Room Temperature," *Proceedings of the International Electron Device Meeting*, Dec. 5–8, 1993; pp. 175–177.

* cited by examiner

Primary Examiner—Constantine Hannaher
(74) Attorney, Agent, or Firm—Carlton H. Hoel; W. James Brady; Frederick J. Telecky, Jr.

(57) ABSTRACT

An array of bolometers suspended over a substrate by support arms located beneath the corresponding bolometer to allow maximum fill factor in the array.

9 Claims, 34 Drawing Sheets

TOP VIEW OF VIA 1925

BEFORE ETCHING VIA

PARTIALLY ETCHED

AFTER VIA ETCHING

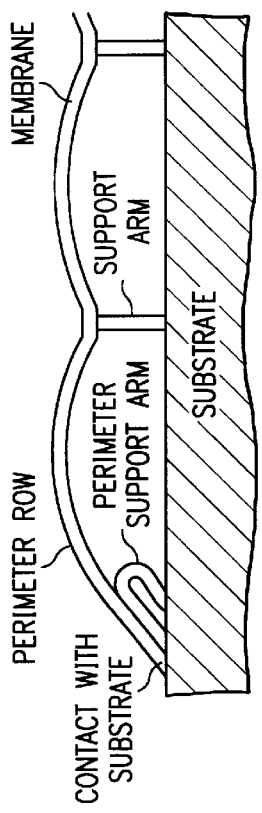
FIG. 21d
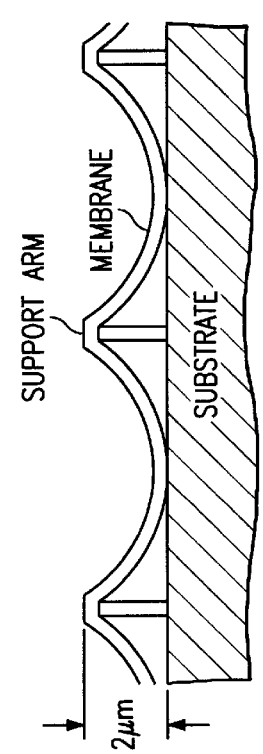
FIG. 21e
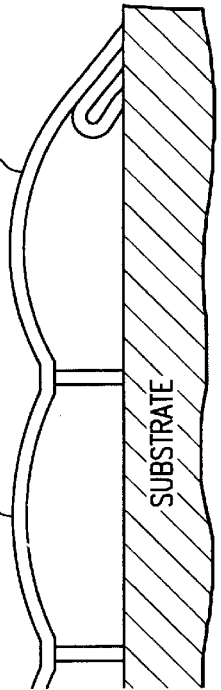
FIG. 21f
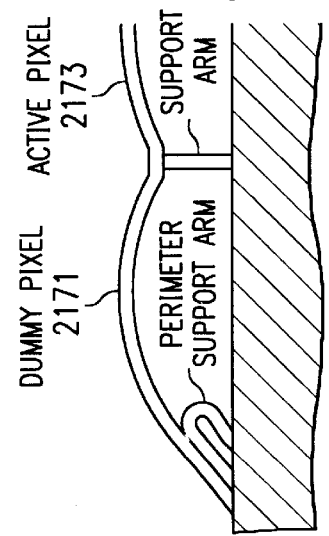

HIGH FILL FACTOR BOLOMETER ARRAY

CROSS-REFERENCE TO RELATED APPLICATIONS

This application claims priority from provisional application Ser. No. 60/001,331, filed Jul. 21, 1995. The following co-filed and copending patent applications disclose related subject matter and are assigned to the assignee of this application: U.S. patent application Ser. Nos. 08/684,601 (now abandoned); 08/684,654 (now U.S. Pat. No. 6,028,312); 08/684,606 (now abandoned); 08/683,997 (now U.S. Pat. No. 5,777,329); 08/690,277 (now abandoned); 08/684,605 (filed Oct. 24, 1996, now abandoned); 08/684,157 (now U.S. Pat. No. 5,841,137); 08/684,600 (now abandoned); 08/684,367 (now U.S. Pat. No. 5,789,753); 08/690,273 (now abandoned); 08/684,121 (now abandoned); 08/684,959 (now abandoned); 08/684,122 (now U.S. Pat. No. 6,064,066); 08/690,276 (now abandoned); and 08/690,275 (now U.S. Pat. No. 5,777,328).

BACKGROUND OF THE INVENTION

The invention relates to electronic devices, and, more particularly, to radiation detectors and systems such as sensors which incorporate such detectors.

Detection of infrared radiation provides important approaches to night vision (imaging based on warm body emissions), chemical analysis (spectral absorption), and various other fields. Infrared detectors may be classified in various ways, such as single detector or pixel arrays, cryogenic (typically liquid nitrogen temperatures) or uncooled detectors, 8–12 mm or 3–5 mm or other wavelength sensitivity, and photon or thermal detection mechanism.

Photon detection (photoconductors, photodiodes, and photocapacitors) functions by photon absorption generating electron-hole pairs in small bandgap semiconductor materials; this increase in the number of electrical carriers is detected. In contrast, thermal detection functions by electrical resistivity or capacitance changes due to the heating of an element absorbing infrared photons. Detectors relying upon the change in resistivity due to photon heating are called bolometers.

Hombeck, U.S. Pat. No. 5,021,663 and Keenan, U.S. Pat. No. 5,288,649 disclose an array of amorphous silicon bolometers suspended over and connected with CMOS control and drive circuitry in the form of a single semiconductor integrated circuit as could be used for night vision. In particular, FIG. 1a schematically illustrates lens system 102, array of bolometers 106, and circuitry for infrared imaging; FIG. 1b heuristically shows the circuitry of a single bolometer, and FIG. 1c shows a portion of an array of bolometers 140. Each bolometer provides the signal for a single pixel in a two-dimensional image. The bolometer suspension over the integrated circuit substrate provides thermal isolation but also engenders mechanical support problems. Bolometer packaging also presents problems because ambient atmosphere may provide thermal coupling of the bolometer with its surroundings and closely spaced detectors lead to crosstalk.

In FIG. 1b $R_B$ denotes the temperature variable resistance, $R_L$ a temperature independent load resistance, and +V a bias voltage applied across $R_B$ and $R_L$ in series for a single bolometer. The temperature variance of $R_B$ due to the varying infrared radiant power input during night vision applications typically is less than one degree Kelvin. The fluctuating temperature of $R_B$ implies a fluctuating resistance which induces a fluctuating voltage across load resistance $R_L$, and this voltage drives the output amplifier. In general, the low frequency noise of the bolometer exceeds the Johnson noise associated with $R_B$ (white noise with amplitude proportional to the resistance) and increases in magnitude with the bias voltage applied across $R_B$. Furthermore, the magnitude of the signal detected by $R_B$–$R_L$ in series is proportional to the bias voltage. And often a bias sufficient to produce a measurable signal produces an unacceptable level of low frequency noise.

Infrared photoconductor detectors also typically have excessive low frequency noise. The usual approach to overcome this low frequency noise problem utilizes chopping (periodically mechanically blocking) the input radiation to measure the output for both irradiated and dark conditions, and then subtracting the dark condition output from the irradiated condition output to provide a net output ("correlated double sampling"). Such chopping greatly attenuates the effects of low frequency noise and improves the signal to noise ratio of the detector.

However, the chopped input approach has problems including the high-cost and low-reliability of mechanical systems. Further, thermal detectors such as bolometers require a substantial scene setting time in order to faithfully represent the signal level. For example, it is not uncommon for bolometers to require a signal interval of 30 milliseconds for faithful signal reproduction. Thus a maximum scene chopping frequency exits. But the effectiveness of correlated double sampling depends upon the scene chopping frequency being greater than the "1/f knee" frequency in the noise power spectrum of the detector. Thus mechanical chopping is not always an effective mechanism because the maximum scene chopping frequency due to scene settling time may be less than the 1/f knee frequency.

Bolometers and photoconductors may also detect visible light and near ultraviolet light and need not be limited to infrared applications; for example, colorimetry applications are just different wavelength applications.

Wong, U.S. Pat. No. 5,163,332 and Burough et al., U.S. Pat. No. 4,709,150 illustrate the use of infrared detectors to detect $CO_2$ or other gases in the atmosphere by measuring absorption in a spectral line by the gas.

SUMMARY OF THE INVENTION

The present invention provides bolometers with multiple wavelength pixel arrays, electronic chopping and autocalibration, internal shade within a vacuum package of multiple detectors, pixel redundancy, close packed bolometers with common supports and hidden supports, ramped foot supports for suspended bolometers, and gas sensors with an infrared source plus bolometer detectors for spectral analysis.

The advantages of the invention include: Multiple detectors with differing filters permits multiple band detection and thus an integrated sensor for multiple gases. Close packed and redundant bolometers yields increased sensitivity, and ramped foot supports provides mechanical strength for suspended bolometers. Internal shade with widely spaced detectors limits cross talk in a compact package. Electronic chopping has advantages including elimination of mechanical chopping plus the avoidance of scene settling time as a frequency limitation on chopping frequency.

BRIEF DESCRIPTION OF THE DRAWINGS

The drawings are schematic for clarity.

FIGS. 21a–g are plan views of preferred embodiment arrays of pixels.

DESCRIPTION OF THE PREFERRED EMBODIMENTS

Two-component pixel preferred embodiment

Figure 2A:
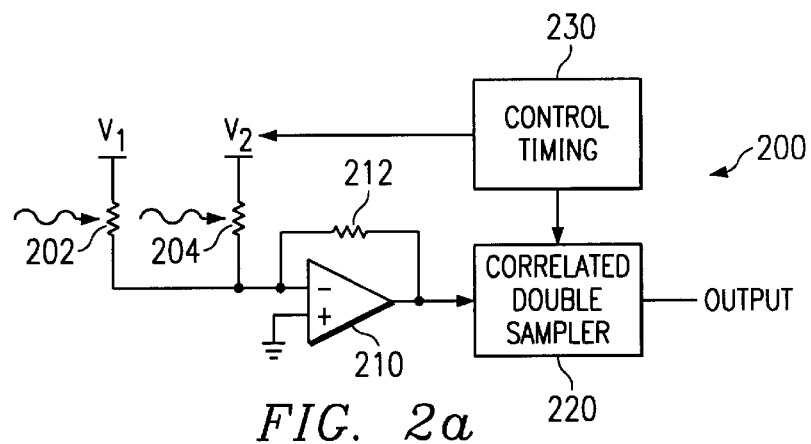
FIGS. 2a–b schematically show in block format first preferred embodiment electronically chopped detector.
Figure 2B:
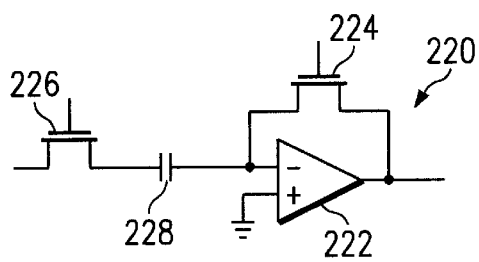

FIGS. 2a–b illustrate in schematic form a two-component resistive element preferred embodiment detector, generally denoted by reference numeral 200, as including photoconductors 202 and 204, operational amplifier 210 with feedback resistor 212, correlated double sampler 220, and timing and bias control 230. Photoconductors 202 and 204 may be made as two portions of a single resistive film of amorphous silicon 306 as shown in plan view in FIG. 3a and cross sectional elevation view in FIG. 3b. Metal contact 310 divides film 306 into two equal portions with metal contacts 312 and 314 on the ends of film 306 and parallel to metal contact 310. The metal contacts are made of aluminum or other metal such as nickel. Contacts 310 and 312 plus the portion of film 306 between them forms photoconductor 202, and contacts 310 and 314 plus the portion of film 306 between them forms photoconductor 204. Film 306 is 50 $\mu$m by 50 $\mu$m and 200 nm thick and on silicon dioxide ("oxide") layer 304 which in turn is on silicon substrate 302. The resistance of photoconductors 202 and 204 are both equal roughly to 20 megohms in the dark and 1% lower in a flux of $5\times10^{-4}$ watts/cm$^2$ of photons with wavelength of 0.3–1.2 mm. Detector 200 could be one pixel in an array of pixels for image detection or as a single detector in a chemical analyzer. The same circuitry could be used with bolometers in place of the photoconductors. Bolometers are useful for detection in the infrared spectrum (e.g., 1–20 mm wavelengths) because a photoconductor would require a narrow bandgap material such as HgCdTe and incorporation of such materials in a silicon integrated circuit would present problems.

Figure 3A:
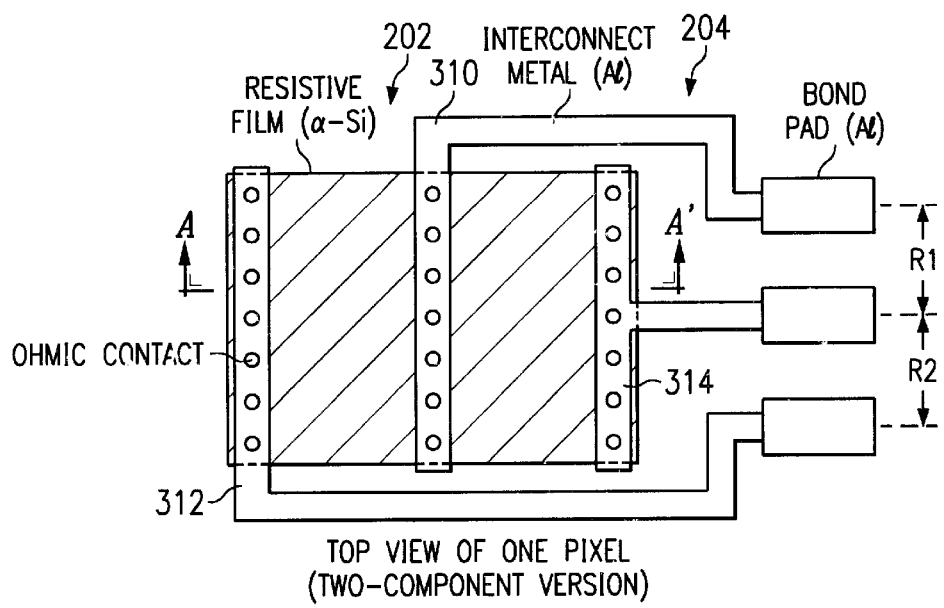
FIGS. 3a–b are plan and cross sectional elevation views of a pixel of the first preferred embodiment.
Figure 3B:
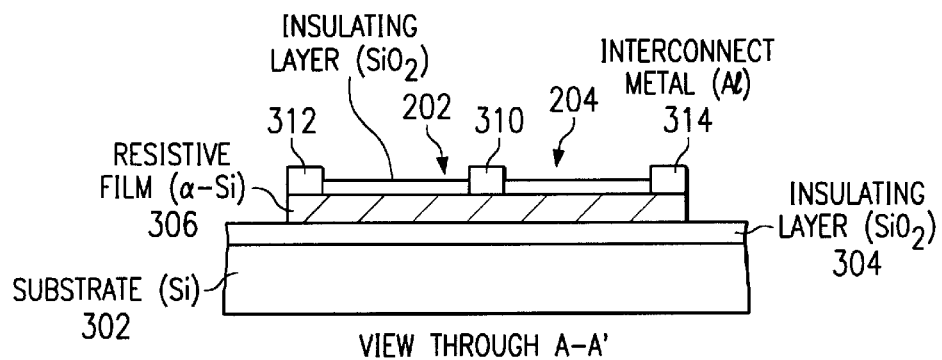

The detector circuitry connected to the radiation sensitive elements is preferably integrated on the same silicon substrate 302 but is not shown in FIGS. 3a–b for clarity. Similarly, the supporting circuitry for the other embodiments also will not be explicitly shown.

Figure 4:
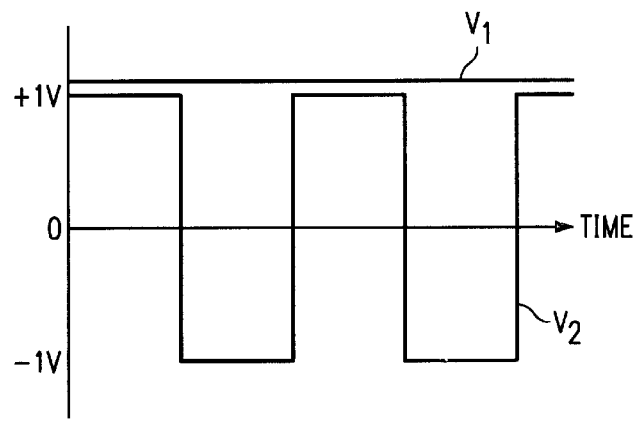
FIG. 4 is a timing diagram.

A lens system focuses the radiation from a scene to be detected onto an array of detectors 200, and each detector 200 operates (synchronously) as follows. The radiation constantly illuminates photoconductors 202 and 204; thus there is no scene settling time to impose an upper limit to frequency, especially for an embodiment with photoconductors 202 and 204 replaced with bolometers. However, control and timing 230 applies a constant bias of +1 volt to contact 312 and a bias switching between +1 volt and −1 volt to contact 314; see the timing diagram of FIG. 4. Common contact 310 connects to the inverting input of operational amplifier ("opamp") 210, which is at virtual ground. Thus when a bias of +1 volt applies to contact 314, photoconductors 202 and 204 both have the same applied voltage and the currents through the photoconductors add and pass through feedback resistor 212 to the output of opamp 210 which will thus be at $-2VR_{212}/R_{PH}$ where $R_{PH}$ denotes the common resistance of photoconductors 202 and 204. Contrarily, when a bias of −1 volt applies to contact 314, photoconductors 202 and 204 have equal magnitude but applied voltages of opposite polarity. Thus the currents from the two photoconductors cancel at the inverting input of opamp 210, and no current flows through feedback resistor 212, and the opamp output will be $V_0$ which is 0.

Figure 1A:
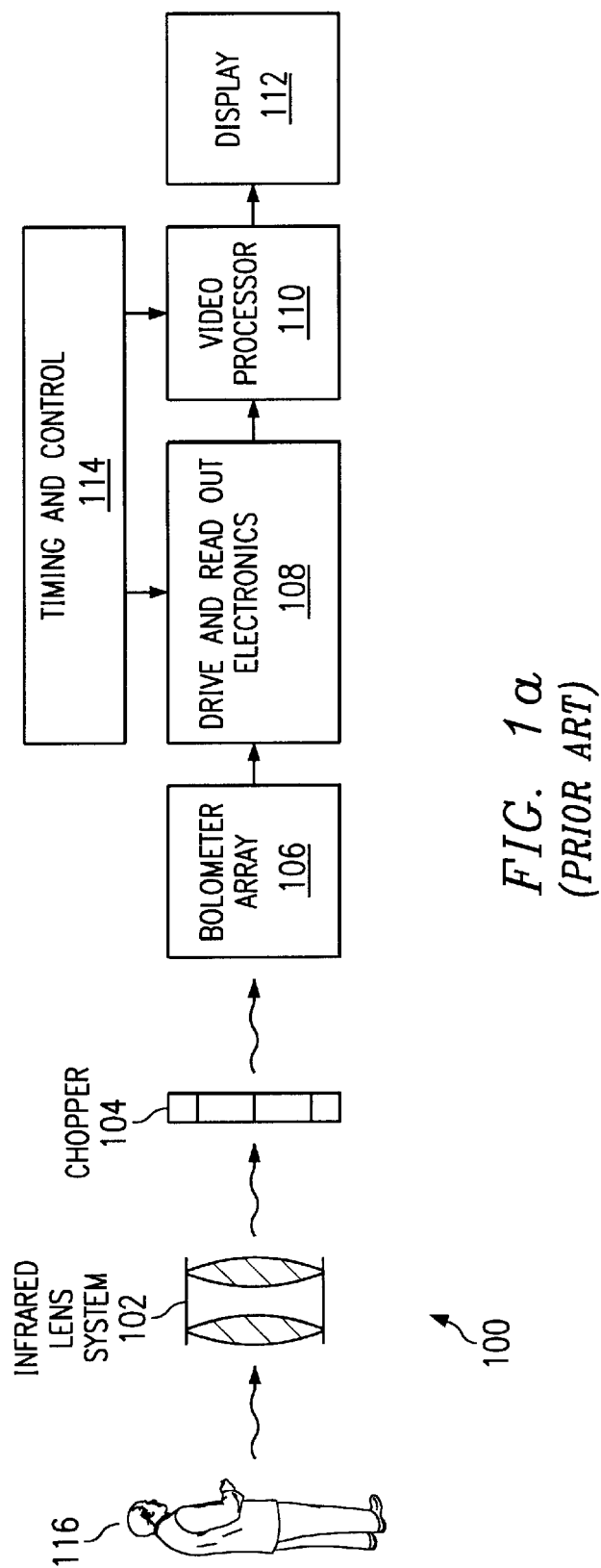
FIGS. 1a–c show known bolometer systems.

Correlated double sampler 220 takes the output of opamp 210 and subtracts the opposite-polarity output from the same-polarity output for successive bias polarity switched intervals. The result is a scene-independent dc offset and an ac signal proportional to the incident scene radiation. This electronic bias switching and correlated double sampling greatly attenuates low-frequency noise just as mechanical chopping and correlated double sampling does. The output of opamp 210 thus emulates that of the amplifier of FIG. 1a with a chopped input with the frequency of bias polarity switching corresponding to the chopping frequency. That is, this bias switching achieves an electronic chopping.

FIG. 2b illustrates correlated double sampler 220 as including opamp 222 with clamping switch 224 and input switch 226 and capacitor 228. Switches 224 and 226 may be MOSFET transistors. Control-ting block 230 may use a ring oscillator to provide the timing signals for the bias polarity switching and for sampling and clamping by correlated double sampler 220. The output of correlated double sampler 220 will be at one-half the bias switching frequency and will be a stream of analog values representing a dc offset due to the bias current through resistances 202 and 204 plus a varying signal due to the varying input radiation. In particular, correlated double sampler operates as follows: first, during a period of photoconductors 202 and 204 with opposite polarity biases, switches 224 and 226 are pulsed closed; this charges capacitor 228 to $V_O$ and the output of opamp is zeroed. Then during a period of photoconductors 202 and 204 with the same polarity biases, switch 226 is pulsed dosed; this changes the input to capacitor to $2VR_{212}/R_{PH}$ and thus the input to the inverting input of opamp 222 to $2VR_{212}/R_{PH}-V_0$ and the opamp output to $A(2VR_{212}/R_{PH}-V_0)$ where A is the amplification.

Note that the current through photoconductor 214 does not change magnitude but only polarity thus no scene settling time is needed, and the chopping frequency will only be limited by the capacitance of the structure.

Detector 200 used equal resistance plus equal optical responsivities in resistances 202 and 204 together equal magnitude bias voltages. However, the switching of bias polarity also provides noise suppression even after relaxing these presumptions. Nonequalites in the resistances, optical responsivities, or bias magnitudes affect the net responsivity of the detector and the offset pedestal, but does not alter the noise performance.

Detector 200 could also use bolometer elements in place of photoconductors with the same analysis.

Four-component pixel preferred embodiment

Figure 5:
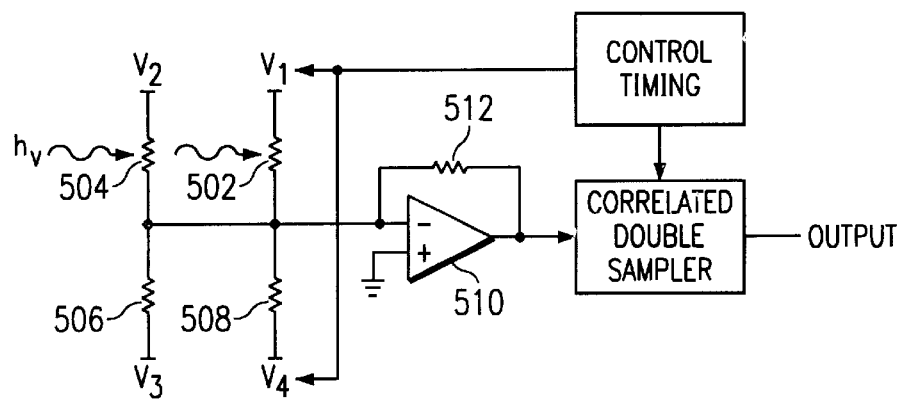
FIG. 5 schematically shows second preferred embodiment detector.
Figure 6A:
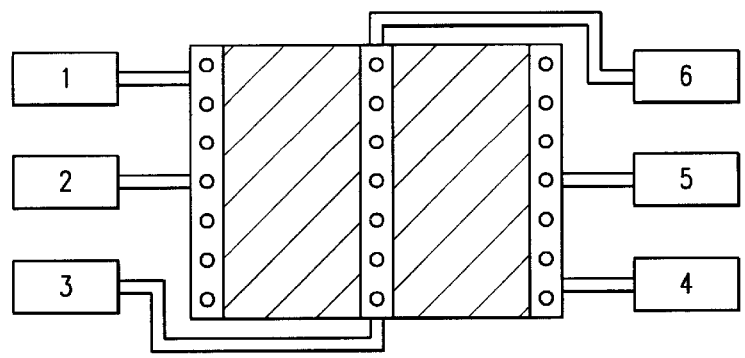
FIGS. 6a–b are plan and cross sectional elevation views of a pixel of the second preferred embodiment.
Figure 6B:
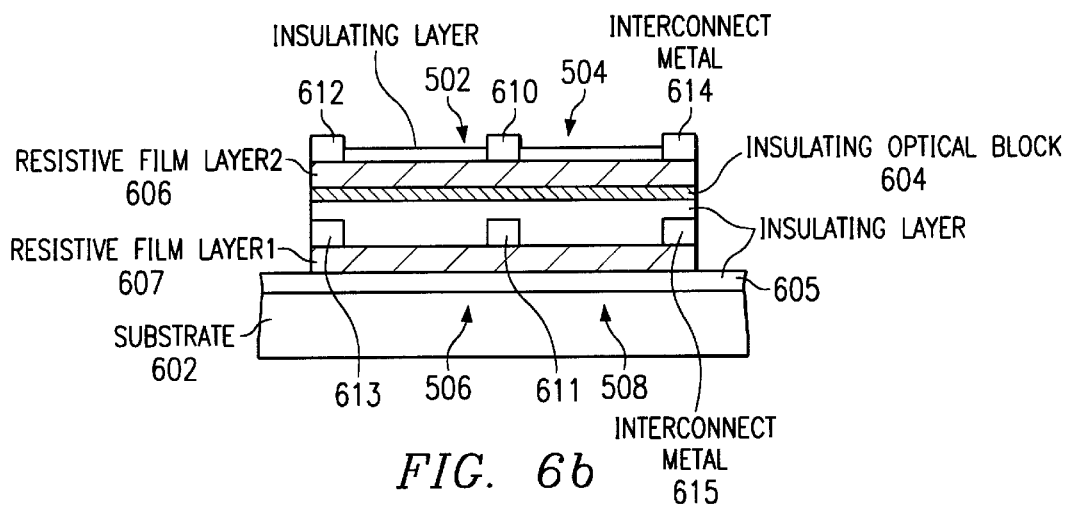

Detector 200 has a bias-current induced dc offset at the output of opamp 210. FIG. 5 illustrates in schematic form a four-component resistive element preferred embodiment detector 500 which avoids the dc offset. In particular, detector 500 includes photoconductors 502, 504, 506, and 508 with photoconductors 502 and 504 receiving input radiation and photoconductors 506 and 508 being shielded from the input, and opamp 510 with feedback resistor 512, correlated double sampler 520, and control and timing 530. Again, detector 500 could be one pixel of an array of pixels in an imager or a single detector, and the photoconductors could be replaced with bolometers.

Photoconductors 502–504 may be made as two portions of a single resistive film of amorphous silicon 606 and photoconductors 506–508 may be made as two portions of another single resistive film of amorphous silicon 607 located under film 606 and thereby shielded from input infrared radiation as shown in plan view in FIG. 3a and cross sectional elevation view in FIG. 3b. Metal contact 610 divides film 606 into two equal portions with metal contacts 612 and 614 on the ends of film 606 and parallel to metal contact 610. The metal contacts are made of aluminum. Contacts 610 and 612 plus the portion of film 606 between them forms photoconductor 502, and contacts 610 and 614 plus the portion of film 606 between them forms photoconductor 504. Similarly, contact 611 divides film 607 into two equal portions and photoconductor 506 includes the film between contacts 611 and 613 and photoconductor 508 includes the film between contacts 611 and 615. Films 606 and 607 may each be 50 mm by 50 mm and 200 nm thick and film 607 lies on oxide layer 605 which in turn is on silicon substrate 602. Film 606 in turn lies on insulating layer 604 which also blocks input radiation and could be made of alumina. The resistance of each of photoconductors 502–508 equals roughly 20 megohms in the dark.

Figure 7:
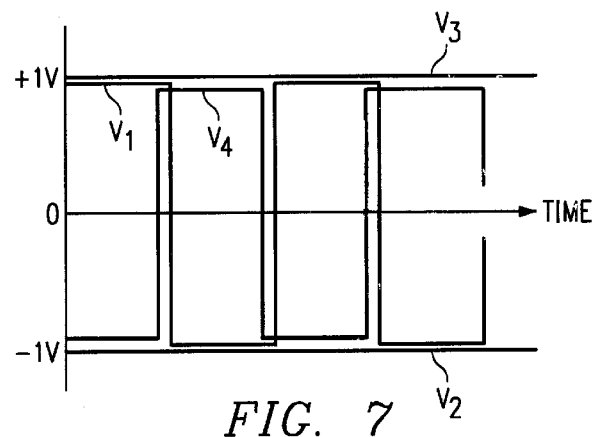
FIG. 7 is a timing diagram.

FIG. 7 shows the bias voltages ($V_1$, $V_2$, $V_3$, and $V_4$ in FIGS. 5 and 7) applied to the four photoconductors. Photoconductors 502 and 504 which receive the input radiation have relative bias polarity switching analogous to photoconductors 202 and 204 of detector 200: switching between +1 volt and −1 volt at a "chopping" frequency for photoconductor 502 and a steady −1 volt for photoconductor 504. Shielded photoconductors 506 and 508 also have relative bias polarity switching which is synchronized with that of photoconductors 502 and 504: the bias of photoconductor 508 switches between −1 volt and +1 volt and the bias of photoconductor 506 remains a steady +1 volt.

Detector 500 operates analogously to detector 200: first consider the case of the bias on photoconductor 502 as +1 volt (so it has opposite polarity of the bias on photoconductor 504) and the bias on photoconductor 508 is −1 volt (so its has opposite polarity of the bias on photoconductor 506). Then the currents in the two photoconductors receiving input radiation (502 and 504) have the same magnitude but opposite polarity and contribute 0 current to feedback resistor 512. Similarly, the currents in the two shielded photoconductors (506 and 508) also have the same magnitude and opposite polarity and also contribute 0 current to feedback resistor 512. Consequently, the output of opamp 520 is 0.

Next, consider the case of same polarity biases. Photoconductors 502 and 504 have the same polarity bias (−1 volt) and provide a current of $-2V/R_{502-504}$ to feedback resistor 512; and photoconductors 506 and 508 have the same polarity bias (+1 volt) and provide a current of $2V/R_{506-508}$ where $R_{502-504}$ is the resistance of each of photoconductors 502 and 504 and $2V/R_{506-508}$ is the resistance of each of shielded photoconductors 506 and 508. Now when there is no input radiation impinging photoconductors 502 and 504, they have the same resistance as shielded photoconductors 506 and 508, so $R_{502-504}$ equals $R_{506-508}$ and the current to feedback resistor 512 is 0. However, when input radiation impinges on photoconductors 502 and 504, then $R_{502-504}$ is less than $R_{506-508}$ and the four photoconductors provide a net negative current to feedback resistor 512 with the current proportional to the input radiation intensity. Indeed, if R denotes the common resistance of the photoconductors in the dark, and if a is the (small) fractional decrease in resistance due to input radiation, then the current through the feedback resistor is 2Va/R and the output proportional to the input radiation.

Figure 8A:
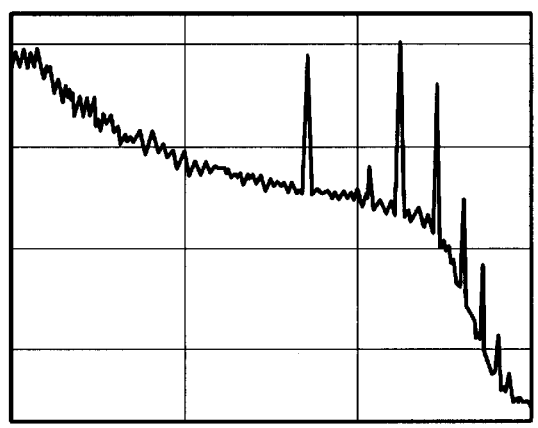
FIGS. 8a–c illustrate noise suppression.
Figure 8B:
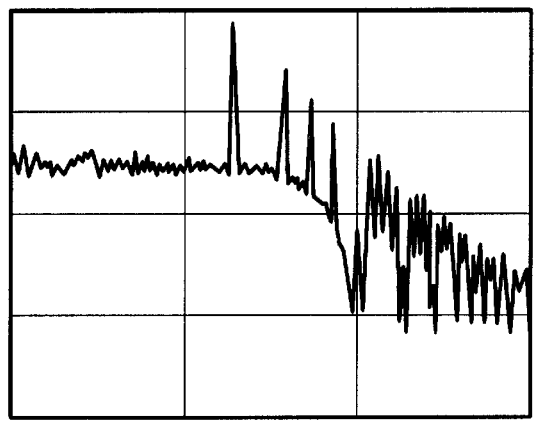
Figure 8C:
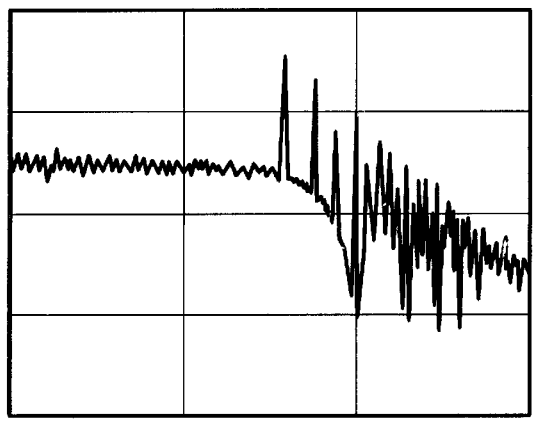

When the four photoconductors do not have the same dark resistances due to mismatches or the positive and negative biases to not match or the elements have different optical responsivities, detector 500 still obtains the same low frequency noise suppression emulating mechanical chopping. FIGS. 8a–c illustrates experimental results: FIG. 8a shows the noise spectrum obtained from detector 500 with a steady bias of 1 volt on all photoconductors, filtered by a 3 dB per octave lowpass filter with 300 Hz bandwidth, and without any correlated double sampling. The excess 1/f low frequency noise appears with a frequency knee at about 100 Hz. FIG. 8b shows the noise spectrum again with a steady 1 volt bias on all photoconductors filtered by a 3 dB per octave lowpass filter with 300 Hz bandwidth but after correlated double sampling; thus this is the minimum noise due to Johnson noise and would be obtained if the scene were mechanically chopped. Lastly, FIG. 8c shows the noise spectrum with electronic chopping as described (bias switching between −1 volt and +1 volt on two of the photoconductors). FIG. 8c and FIG. 8b are virtually identical; this demonstrates that the additional bias switching required for the electronic chopping does not affect the excess or Johnson noise components of the detector. This reflects the fact that the bias is being switched but not changed in magnitude, so the power is not changed.

Alternate two-component pixel preferred embodiment

Figure 9A:
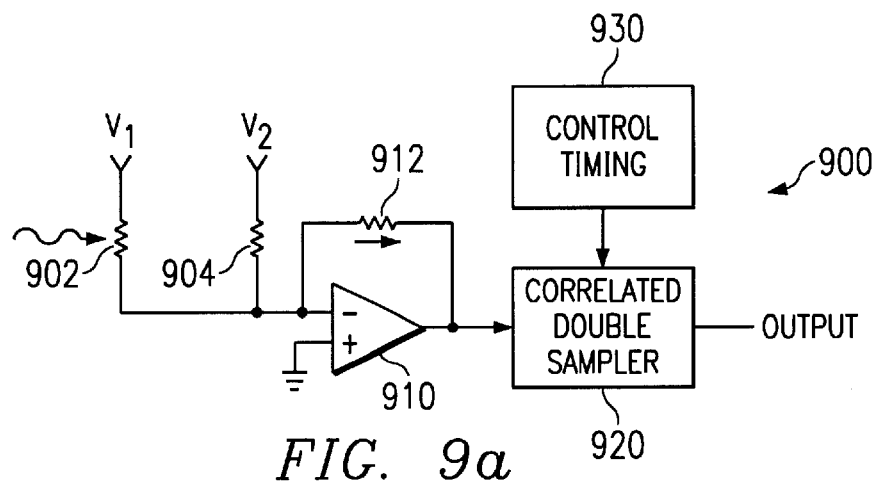
FIGS. 9a–b schematically show in block format another preferred embodiment electronically chopped detector.
Figure 9B:
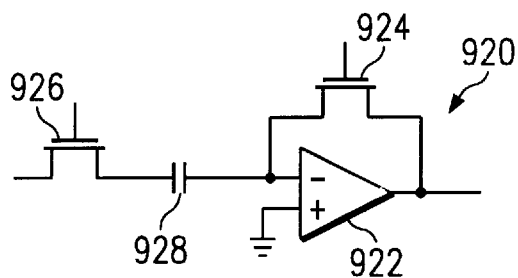

FIGS. 9a–b illustrate in schematic form another two-component resistive element preferred embodiment radiation detector, generally denoted by reference numeral 900. Detector 900 includes photoconductor 902 receiving input radiation, otoconductor 904 shielded from input radiation, opamp 910 with feedback resistor 912, correlated double sampler 920, and timing and bias control 930. Photoconductors 902 and 904 are made from two electrically isolated resistive films 1006 and 1012 of amorphous silicon as shown in plan view in FIG. 10a and cross sectional elevation view in FIG. 10b. Metal contacts 1014 and 1016 provide electrical contacts for photoconductor 902, and metal contacts 1018 and 1020 provide electrical contacts for photoconductor 904. Films 1006 and 1012 each are 50 $\mu$m by 50 $\mu$m and 500 nm thick, and film 1006 lies on oxide layer 1004 which in turn is on silicon substrate 1002. Film 1012 in turn lies on alumina insulating layer 1010 which blocks any scene radiation penetrating film 1012. Alumina film 1010 lies on an additional insulating oxide layer 1008. The dark resistance of each photoconductor 902, 904 is roughly 50 megohms. Again, bolometers could be used in place of photoconductors.

Figure 11:
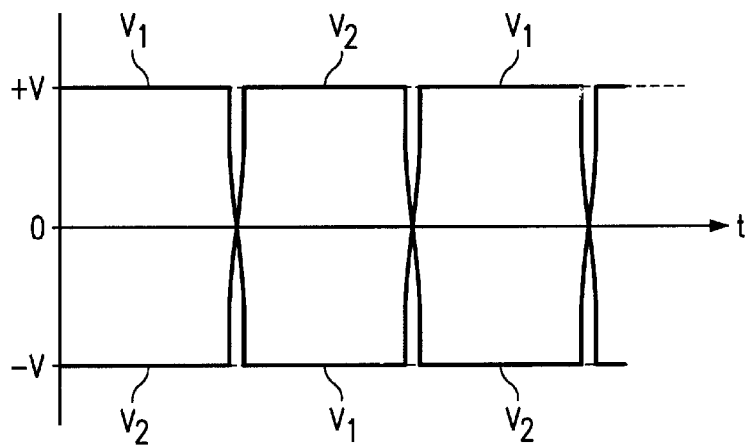
FIG. 11 is a timing diagram.

FIG. 11 shows the bias voltages $V_1$, $V_2$ applied to the two photoconductors 902, 904. Both photoconductors have relative bias polarity switching between +V and −V volts at the same "chopping" frequency analogous to photoconductors 202, 204 of detector 200, but the two biases have a phase difference of 180 degrees.

Detector 900 operates as follows. First, consider the case of the bias on photoconductor 902 as +V volts and the bias on 904 as −V volts. This configuration provides a current of $V/R_{902} - V/R_{904}$ through feedback element 912, where $R_{902}$ and $R_{904}$ are the resistances of photoconductors 902 and 904, respectively. Now with no input radiation on photoconductor 902, $R_{902}$ will equal $R_{904}$ and the current in feedback resistor 912 equals 0. However, with radiation impinging on photoconductor 902, the resistance $R_{902}$ decreases and a net positive current flows through feedback element 912. The current is proportional to the input radiation intensity. Indeed, if R denotes the common resistance of the photoconductors in the dark and if a is the (small) fractional decrease in resistance due to scene radiation, then the current through the feedback resistor is aV/R and the opamp output is proportional (ratio of feedback resistance to R).

Next, consider the case of the bias on photoconductor 902 as −V volts and the bias on 904 as +V volts. This configuration provides a current of $V/R_{904} - V/R_{902}$ through feedback element 912. Again, with no input radiation on photoconductor 902, the feedback element current equals 0, and the opamp output is 0. Conversely, with input radiation on photoconductor 902, the feedback resistor current equals −aV/R and the opamp output is proportional.

Correlated double sampler 920 receives the output of opamp 910 and subtracts the output during one bias configuration from the output during the other bias configuration. Thus correlated double sampler 920 outputs a result proportional to 2aV/R and greatly attenuates the low-frequency noise in a manner analogous to mechanical chopping.

AC-coupled preferred embodiment

Figure 12:
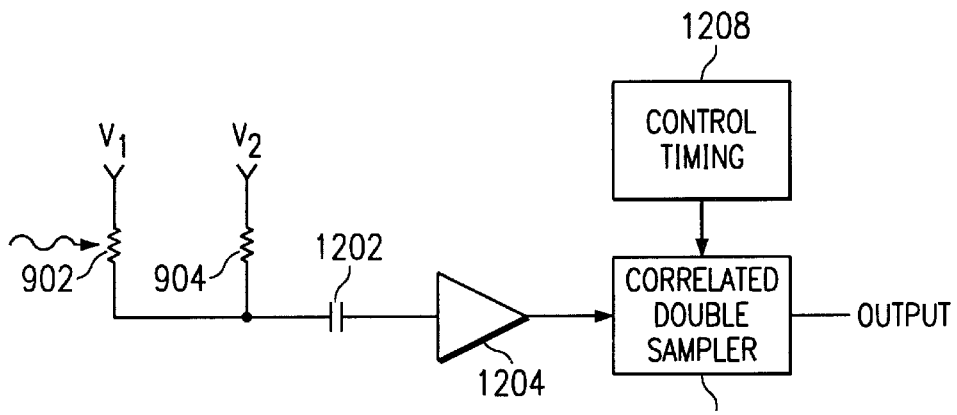
FIG. 12 illustrates ac-coupling of pixel elements.

FIG. 12 illustrates a modified version of detector 900 with photoconductors (or bolometers) 902, 904 coupled through capacitor 1202 to amplifier 1204 and then to correlated double sampler 1206 with controller 1208. This capacitive coupling eliminates the DC offset across the feedback resistor in FIG. 9, which allows the gain of amplifier 1204 to be high. FIG. 11 again shows that the bias voltages $V_1$, $V_2$, applied to photoconductors 902, 904, respectively, simultaneously switch (at a chopping frequency of about 1 KHz) between positive and negative and have opposite polarities. The parallel combination of resistances $R_{902}$ and $R_{904}$ of photoconductor 902 and 904 between bias voltages $V_1$ and $V_2$ and capacitor 1202 develops a voltage of $(V_1-V_2)R_{904}/(R_{902}+R_{904}) - V_2$ at the input side of capacitor 1202. If R denotes the common resistance of photoconductors 902, 904 in the dark, and if a is the fractional decrease in $R_{902}$ due to scene radiation, then the magnitude of the voltage at capacitor 1202 equals $\pm aV/(2+a)$ where V is the magnitude of $V_1$, $V_2$. When the bias on photoconductor 902 is +V and the bias on photoconductor 904 is −V, the voltage at capacitor 1202 equals $+aV/(2+a)$; and when the bias polarities are reversed, the polarity at capacitor 1202 also reverses to $-aV/(2+a)$. Thus with scene radiation impinging on photoconductor 902, the voltage at capacitor 1202 toggles between positive and negative, and correlated double sampler 1206 outputs (presuming amplification of 1 by amplifier 1204) $2aV/(2+a)$. Again, the bias switching provides an electronic chopping and a reduction in low frequency noise. As with the previously described embodiments, mismatches in the dark resistances or bias magnitudes affect the net responsivity of the detector and the offset pedestal, but does not affect the noise reduction afforded by the electronic chopping.

Active feedback preferred embodiment

Figure 13:
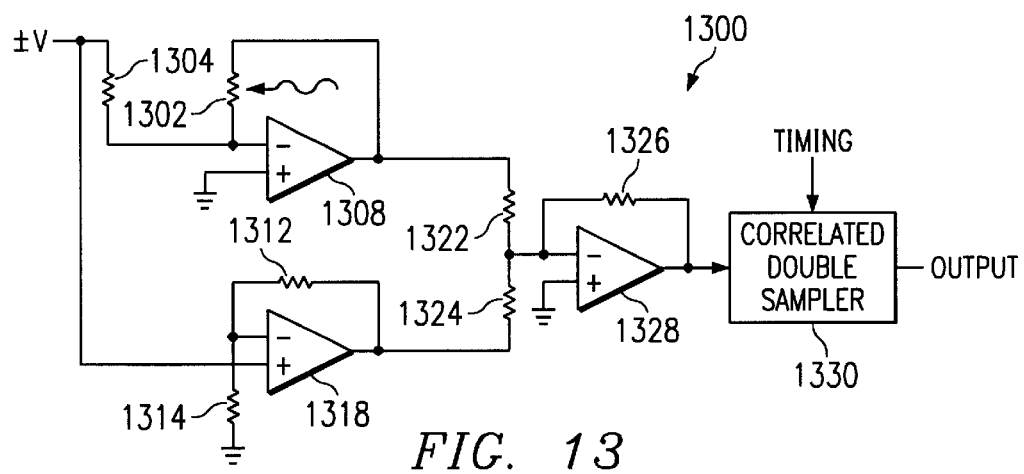
FIG. 13 shows an alternative arrangement of pixel elements.

FIG. 13 illustrates detector 1300 which includes matched bolometers (or photoconductors) 1302 and 1304, opamp 1308, temperature insensitive resistors 1312 and 1314, opamp 1318, temperature insensitive resistors 1322, 1324, and 1326, opamp 1328, and correlated double sampler 1330. The input bias switches between +V and −V at the electronic chopping frequency.

Bolometer resistor 1302 receives input radiation (or has a thermally adjacent radiation absorber) and thereby heats up, whereas bolometer resistor 1304 has a radiation shield. Bolometer resistors 1302 and 1304 have adjacent locations on an integrated circuit substrate so that they have the same thermal inputs and environment except for the radiation heating of resistor 1320. Consequently, with incident radiation, the output voltage of opamp 1308 approximately equals $-V(1+aDT)R_{1302}/R_{1304}$ where a is the fractional increase of resistivity per degree C, DT is the increase in temperature due to the incident radiation, $R_{1302}$ and $R_{1304}$ are the resistances of resistors 1302 and 1304 without any heating. Note that any nonradiation heating or cooling of the resistors 1302 and 1304 will generate the same increase or decrease factor in both resistances and this cancels out.

The output of opamp 1318 equals $\pm V(1+R_{1312}/R_{1314})$ with $R_{1312}$ and $R_{1314}$ the resistances of resistors 1312 and 1314. Opamp 1328 sums the outputs of outputs 1308 and 1318 to feed correlated double sampler 1330; in particular, the output of opamp 1328 is:

$$V_{1328} = -V_{1308}R_{1326}/R_{1322} - V_{1318}R_{1326}/R_{1324}$$

$$= \pm V(R_{1326}/R_{1322})(R_{1302}/R_{1304})aDT +$$

$$\pm VR_{1326}[R_{1302}/R_{1304}R_{1322} - (R_{1314}+R_{1312})/R_{1314}R_{1324}]$$

where the subscripts refer to the items with the same reference numerals. Now one (or more) of resistors 1314, 1312, 1322, and 1324 is variable or trimmable and may be adjusted to make the second term on the righthand side of the foregoing equation vanish, which means the current through 1322 equals that of 1324. For example, with resistor 1324 having its resistance set as:

$$R_{1324}=(R_{1314}+R_{1312})R_{1304}R_{1322}/R_{1302}R_{1314}$$

the output of opamp 1328 is:

$$V_{1328}=\pm V(R_{1326}/R_{1322})(R_{1302}/R_{1304})aDT$$

and correlated double sampler 1330 subtracts the negative bias output from the positive bias output to give an output of $2V(R_{1326}/R_{1322})(R_{1302}/R_{1304})aDT$.

Of course, bolometer element 1304 could receive the input radiation and bolometer element 1302 would be the shielded element. Also, opamp 1308 together with bolometer elements 1302–1304 could be used to directly drive correlated double sampler 1330.

Detector array preferred embodiment

Figure 14A:
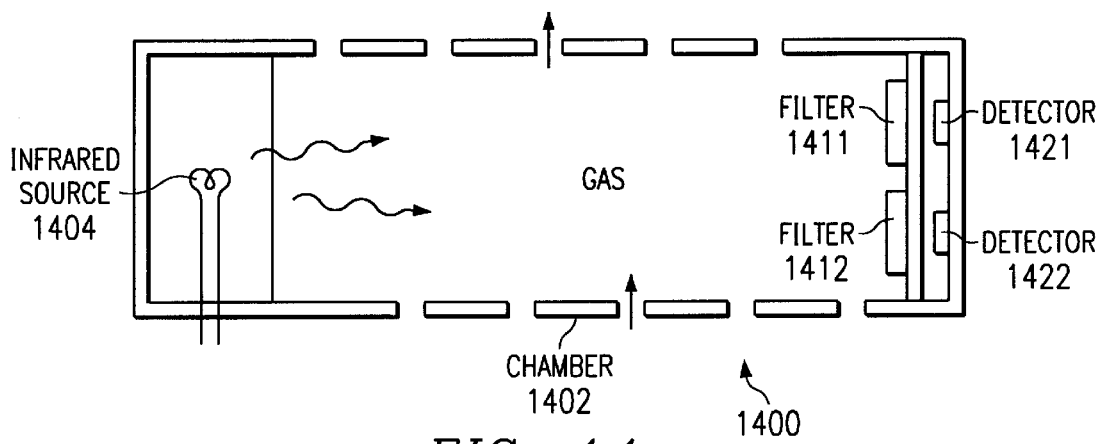
FIGS. 14a–b show a gas sensor application of the preferred embodiments.
Figure 14B:
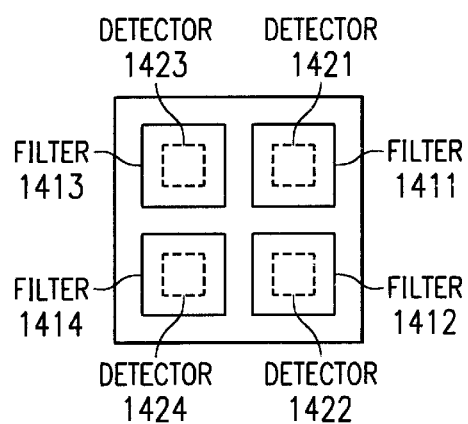

FIGS. 14a–b heuristically illustrate in cross sectional and plan views preferred embodiment environmental gas sensor 1400. In particular, gas sensor 1400 includes chamber 1402, infrared radiation source 1404, four narrow bandpass radiation filters 1411–1414, and four radiation detectors 1421–1424. Detector 1421 is a single pixel detector using a photoconductor or a bolometer made of hydrogenated amorphous silicon and with structure similar to detector 900 and mounted adjacent optical filter 1411. Similarly, each of the other detectors mounts adjacent a corresponding filter. Chamber 1402 blocks outside light from impinging on detectors 1421–1424 and has perforations to permit gas to flow through as indicated by the arrows so that the contents of chamber 1402 reflect the ambient gas composition. Infrared radiation source 1404 may simply be a low wattage light bulb. Filters 1411–1414 are multilayered interference bandpass filters with bandwidths of about 0.2 mm The resistance of hydrogenated amorphous silicon for bolometer use decreases about 3% per degree C at room temperature.

Gas sensor 1400 detects the presence of three gasses: carbon dioxide, water, and volatile organic compounds (VOC) as follows. Filter 1411 has a passband centered at a wavelength of 4.26 μm; this corresponds to an absorption band of carbon dioxide. Filter 1412 has a passband centered at 2.7 μm which is an absorption band of water. Filter 1413 has a passband centered at 3.2 μm; various organic compounds absorb about this wavelength as it corresponds to a C—H stretch bond. Lastly, filter 1414 has a passband centered at 3.6 μm which lies away from absorption by typical atmospheric gasses. Infrared radiation source 1404 emits a broad band of infrared radiation, and detector 1421 will receive the radiation passing through the gas in chamber 1402 and filter 1411. Thus when the carbon dioxide concentration varies in chamber 1402, the radiation received by detector 1421 varies and is detected as previously described. Filter 1411 prevents variation in other gasses in chamber 1402 from affecting the radiation received by detector 1421. Similarly, detector 1422 detects variation in the water vapor concentration in chamber 1402, and detector 1423 detects variation in the VOC concentration Detector 1424 acts as a calibration for detectors 1421–1423 because variations not due to gas concentration changes in chamber 1402, such as variation in the irradiance of source 1404, will be detected by detector 1424. This information can be used to compensate the outputs of detectors 1421–1423.

Details of preferred embodiment components for sensor 1400 appear in the following sections, including a single packaging of detectors 1421–1424 with filters 1411–1414.

Kanthal infrared radiation source preferred embodiment

The first preferred embodiment infrared radiation source 1404 of sensor 1400 includes a wire filament of Kanthal A1 alloy (72% iron, 22% chromium, 5.5% aluminum, and 0.5% cobalt) wound in a coil to give a large area for emission and mounted in a converging reflector. The wire could be 0.1 mm diameter and wound into a cylindrical coil about 2.5 mm in diameter and about 4 mm long. Kanthal alloy wire can be run hot in air as a natural oxide forms which limits further oxidation. The resistivity of Kanthal alloy is almost independent of temperature, so the temperature of operation depends only on the voltage applied. Kanthal alloy also has an emissivity of 0.7 which exceeds that of tungsten, thus it is a more efficient infrared source.

Figure 15:
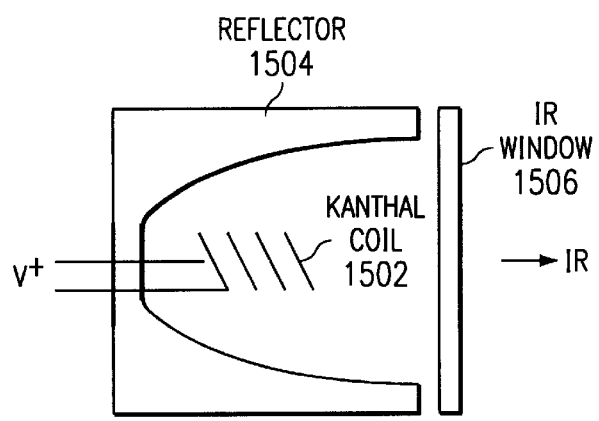
FIGS. 15 and 16a–b schematically illustrate preferred embodiment infrared radiation sources.

FIG. 15 illustrates coil 1502 of Kanthal alloy located about the focus of an ellipsoid of revolution converging reflector 1504 and covered with infrared window 1506 to keep the gas being analyzed from contacting the hot coil 1502. The opening of reflector 1504 and window 1506 can be 25 mm in diameter with a 2 mm space between them to allow for air flow. Reflector has a 40 mm extent and converges a large fraction of the infrared light to a roughly 10 mm diameter area at a distance of 100 mm and with a flux variation of at most 3% across the area. Reflector 1504 with coil 1502 provides a uniform illumination for detectors 1421–1424 and avoids imaging coil 1502 on the detectors which leads to fixed pattern problems. Note that the flux from a coil 1502 located at the focus of a parabolic reflector would be dispersed and less infrared light would reach the detectors. Of course, other converging reflector shapes may also be used provided they produce a uniform flux across the detectors and do not disperse the light.

Coil 1502 will operate in the range of about 500–900° K. (roughly 250–600° C.). Window 1506 could be made of germanium or zinc selenide or other infrared transparent material, and reflector 1502 could be made of any infrared reflector. Higher temperatures imply greater infrared radiation roughly according to $esT^4$, so selection of the applied voltage can adjust for the sensitivity of the detectors 1411–1422.

The Kanthal alloy could be just a surface layer on another supporting structure, and other air oxidation limiting alloys could be used such as nichrome (nickel plus chromium).

Positive Temperature Coefficient Ceramic IR Source

Figure 16A:
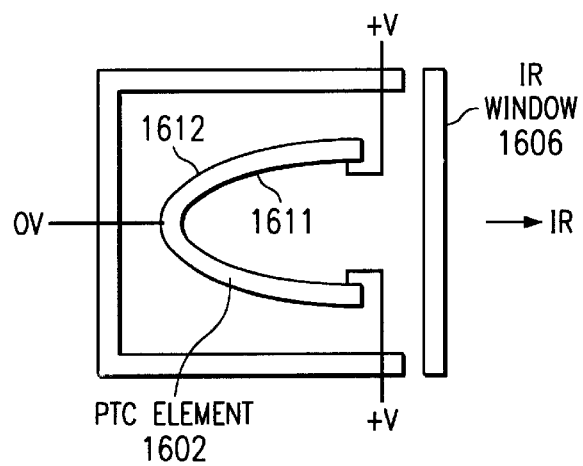
Figure 16B:
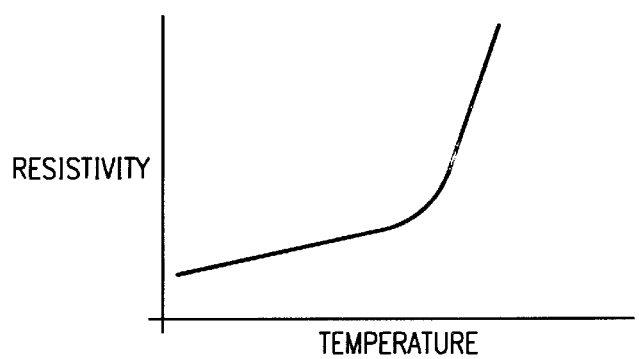

The second preferred embodiment infrared radiation source 1404 of sensor 1400 includes parabola of revolution ceramic disk 1602 with metal coatings 1611 and 1612 as shown in FIG. 16a. Disk 1602 is made of a positive temperature coefficient ceramic (PTC ceramic). These ceramics have significant nonlinear increase in resistivity at fixed temperature which can be selected within the range 500–600 K by adjusting the composition of the ceramic. FIG. 16b illustrates the resistivity as a function of temperature. A voltage applied across the metal coatings 1611–1612 causes conduction through the ceramic and resistive heating until reaching just past the fixed temperature uniformly across disk 1602 at which time the increase in resistivity effectively limits further temperature rise for a broad range of cooling efficiencies. Biased disk 1602 at the fixed temperature thus provides a relatively-easy-to-control stable infrared source.

One problem to solve with infrared sources is the quantity of infrared energy the source emits. One standard solution is to pump a lot of energy into a small filament and allow that filament to get extremely hot and thus give off a reasonable amount of radiation. The same effect can be achieved by using a larger surface area to emit at a cooler temperature. The black body curve will shift more toward the IR and the source will be more efficient in the IR. More of the power into the source will be emitted at the appropriate wavelength for chemical sensing.

The shape of disk 1602 can be varied to increase the emitting surface, although a parabolic shape as shown in the cross section in FIG. 16a provides some directionality for emissions from the interior surface 1611 due to reflections and thus a general directionality as indicated by the arrow labeled IR. The opening of the parabola can be 15 mm in diameter with a 2 mm space to infrared transparent window 1606 to allow for air flow but still provide insulation for the sampled gas. A second possibility is to use a flat source inside a parabolic reflector. This allows use of a commonly manufactured pill shape and still have the amplification effect of a reflector, however the source surface are will be smaller than that of a total reflector shaped PTC source. Lastly, a spherical interior emitting surface 1611 provides some directionality towards the sphere center as suggested by a Huygens wavefront construction.

Another problem to solve is to optimize the surface of the IR source for radiation in the desired range. The preferred embodiment of this source is coated with a dark metal or metal oxide or similar coating like black varnish to increase its emissivity.

The thermal mass of such a device would make a pulsing of the source very difficult. This type of source would be best used with a bolometer with electronic chopping or a mechanical chopper.

Ramp foot bolometer preferred embodiment

Figure 17A:
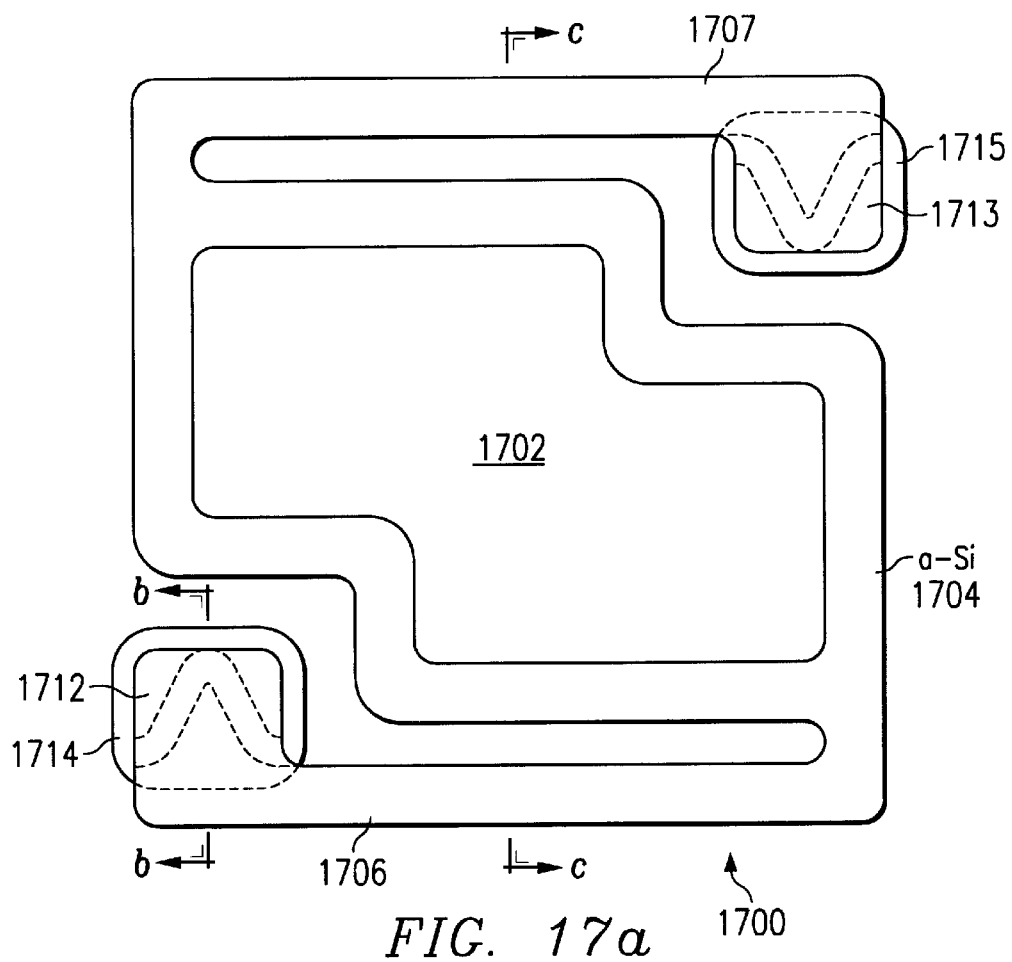
FIGS. 17a–d are plan, cross sectional elevation, and perspective views of a preferred embodiment bolometer.
Figure 17B:
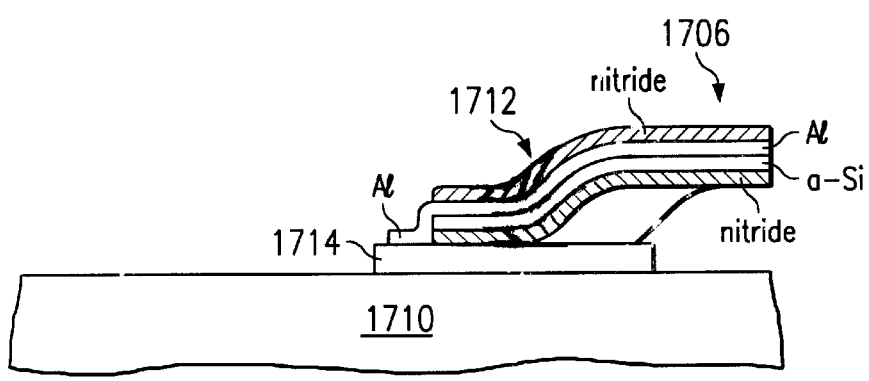
Figure 17C:
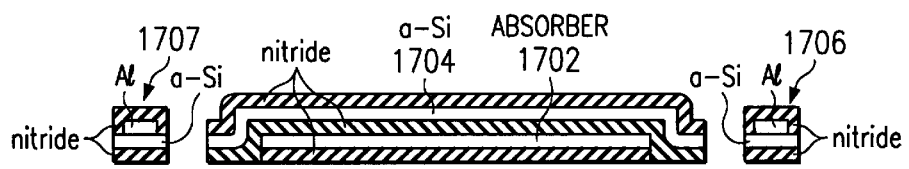
Figure 17C:
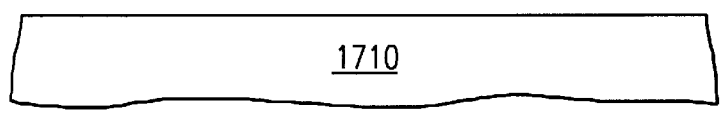
Figure 17D:
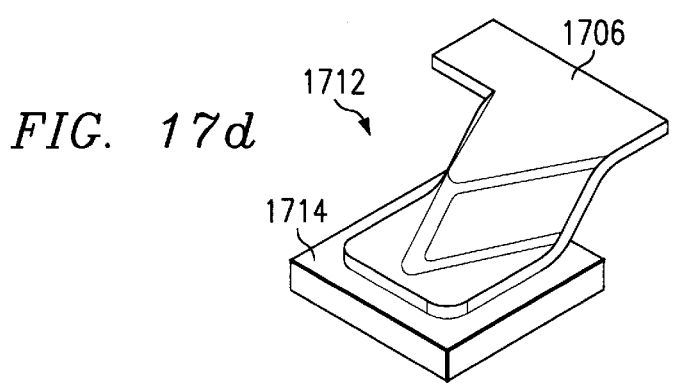

The photoconductor pixels in FIGS. 3a–b, 6a–b, and 10a–b sit directly on the underlying substrate and thus have little thermal isolation from the substrate. FIGS. 17a–d illustrate in plan, cross sectional elevation, and perspective views a preferred embodiment bolometer structure 1700 which suspends the bolometer above the substrate for thermal isolation. In particular, infrared absorber 1702 thermally couples to amorphous silicon temperature dependent resistor 1704 which extends to form thermal isolation support arms 1706–1707 parallel to underlying substrate 1710. Support arms 1706–1707 in turn extend down in the form of ramped feet 1712–1713 to make contact with aluminum pads 1714–1715. Bolometer 1700 has overall outside dimensions of about 50 $\mu$m by 50 $\mu$m, and support arms 1706–1707 suspend absorber 1702 and resistor 1704 about 2 $\mu$m over substrate 1710. Ramped feet 1712–1713 have a roughly 4 $\mu$m long hollow triangular wedge shape as illustrated in perspective view FIG. 17d. A single amorphous silicon layer of thickness 100–200 nm and doped with phosphorus or boron to a resistivity of roughly 150–200 ohm-cm with a silicon nitride ("nitride") coating forms resistor 1704, arms 1706–1707, and ramped feet 1712–1713. FIG. 17b shows a section along line b—b of plan view FIG. 17a and illustrates ramped foot 1712 with FIG. 17d a perspective view of the same ramped foot 1712. Ramped feet 1712–1713 provide strong mechanical attachment to pads 1714–1715. FIG. 17c is the section along line c—c of plan view FIG. 17a and shows support arms 1706–1707 plus absorber 1702 on resistor 1704.

The ramped foot structure can also be used generally for mechanical supports capable of withstanding large lateral force from stress in films or from some purely mechanical structure as in micromachined or micromechanical devices.

Preferred embodiment 1700 operates as follows: absorber 1702 absorbs incident infrared radiation (generally perpendicular to the surface of substrate 1710) and thereby heats up. This heats up resistor 1704 and decreases the resistance. Thus a voltage applied between pads 1714 and 1715 will yield a larger current, and the sampling circuitry previously described detects the increase in current. Similarly, when the incident radiation decreases, absorber 1702 cools off, the resistance increases, the current decreases, and the sampling circuitry detects the decrease.

Absorber 1702 plus resistor 1704 have a thin film structure and thus a small thermal mass per incident radiation area; this provides high sensitivity (degrees increase per incident watt of radiation). Support arms 1706–1707 each has a width of about 2–3 $\mu$m and a length of about 40 $\mu$m and provides thermal isolation of the absorber 1702 plus resistor 1704 structure. When operated in a vacuum, absorber 1702 plus resistor 1704 primarily lose heat by thermal conduction along the support arms from absorber to substrate. If desired, support arms 1706–1707 could be made longer (to increase thermal resistance) by extending along further sides of resistor 1704. Absorber 1702 has a three-layer structure: a 50 nm thick layer of silicon nitride under resistor 1704, a 14 nm thick layer of titanium under the nitride, and a 25 nm thick bottom layer of nitride under the titanium The titanium absorbs infrared, and the nitride provides electrical isolation from resistor 1704 and passivation.

Figure 18:
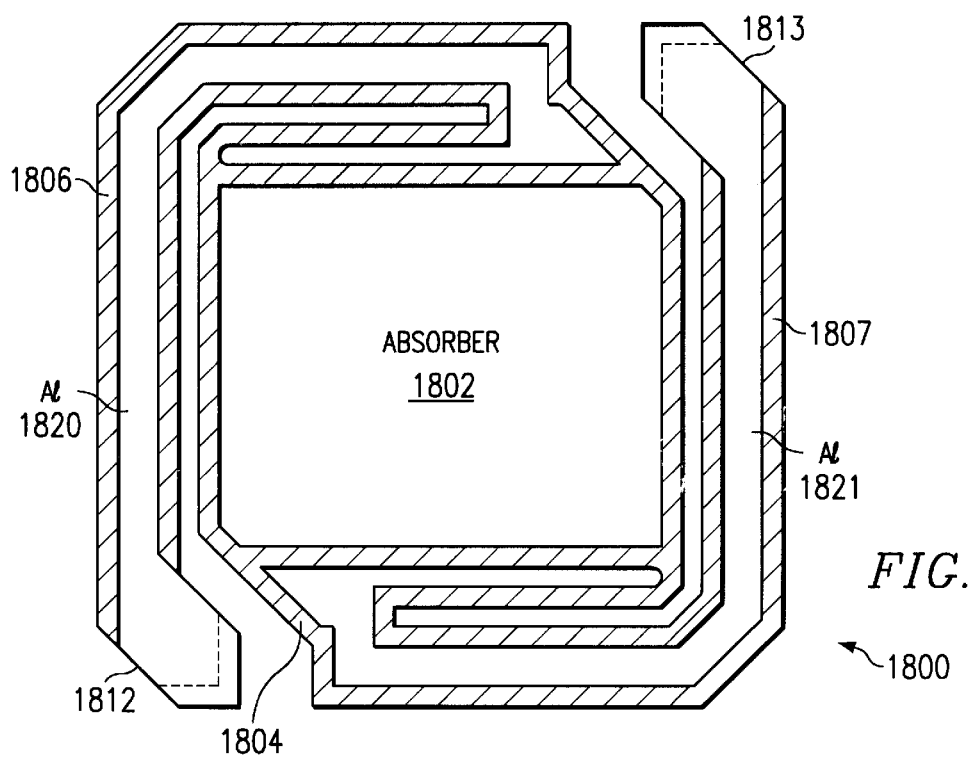
FIG. 18 shows another preferred embodiment bolometer in plan view.
Figure 22A:
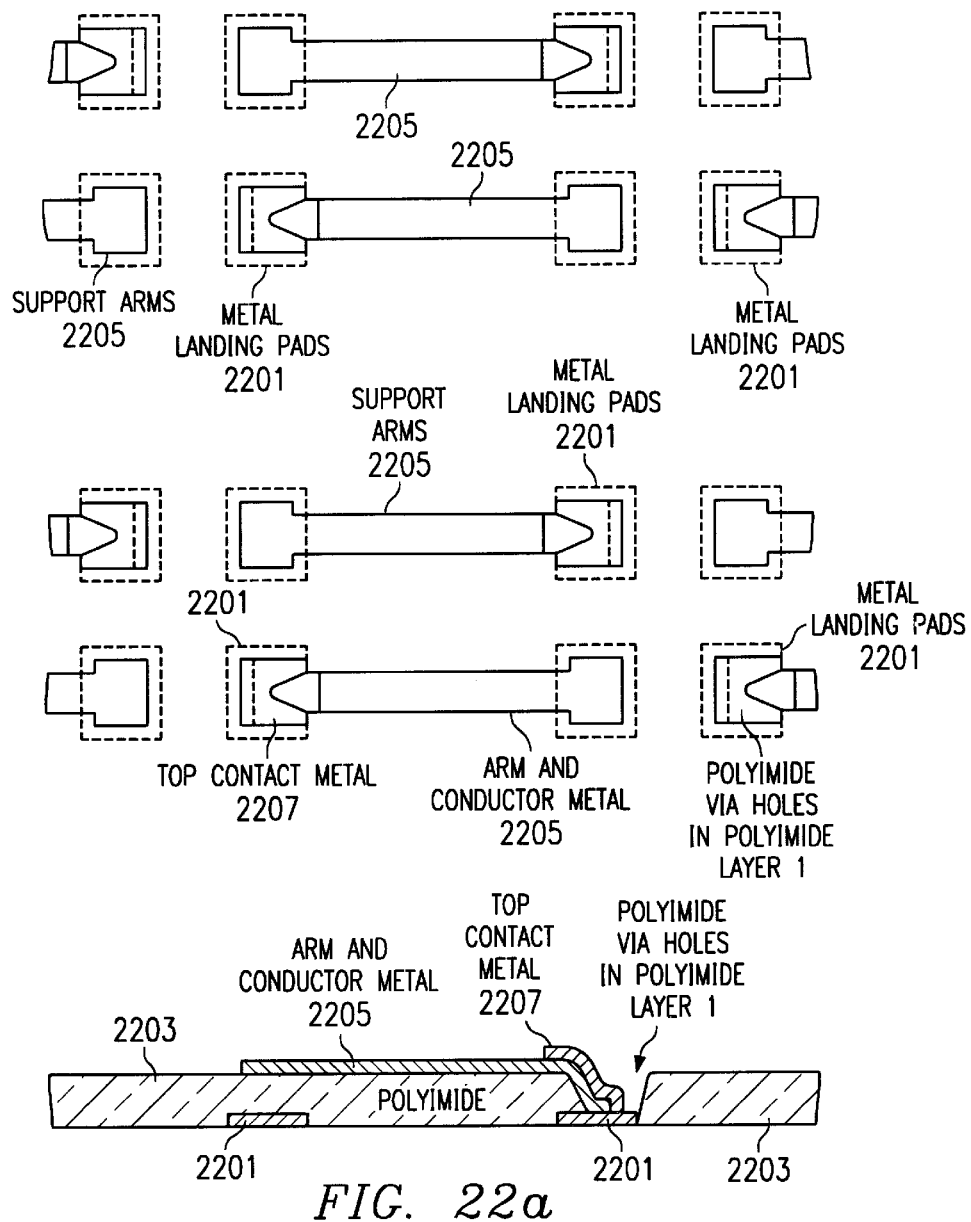
FIGS. 22a–d show a preferred embodiment array of pixels.

In order to minimize the electrical resistance of support arms 1706–1707, a thin (10–20 nm thick) strip (2 $\mu$m wide) of metal, such as aluminum or nickel or titanium or other suitable metal, runs along amorphous silicon-on-nitride ramped foot 1712 onto support arm 1706 and then along one side of resistor 1704 to provide a low resistance electrical path to resistor 1704; see FIGS. 17b–c. A similar metal strip runs from pad 1715 onto ramped foot 1713 along support arm 1707 and along an opposite side of resistor 1704; these metal strips also represent a source of thermal conductance of support arms 1706–1707. FIG. 18 illustrates in plan view bolometer 1800 with metal strips 1820–1821 on support arms 1806–1807 which extend along two sides of resistor 1804 with absorber 1802 for thermal isolation enhanced over those of FIG. 17a and which connect to pads with ramped feet 1812–1813. Because thin metal layers do not cover steps well, a thick metal link (of aluminum) may be formed to cover the ramped foot from pad 1714–1715 up to the top of the foot and out the end of the support arm metal 1820–1821. For example, see metal tab 2207 in FIG. 22a.

Low stress preferred embodiment fabrication

Figure 19A:
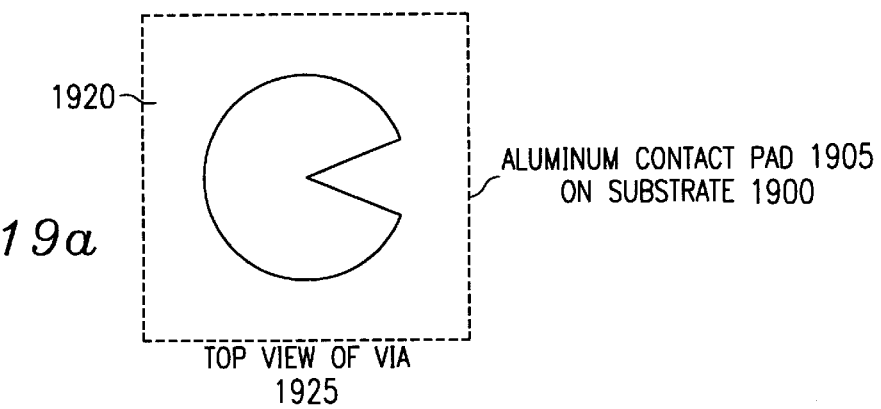
FIGS. 19a–f illustrate steps in a preferred embodiment process for bolometer fabrication.
Figure 19B:
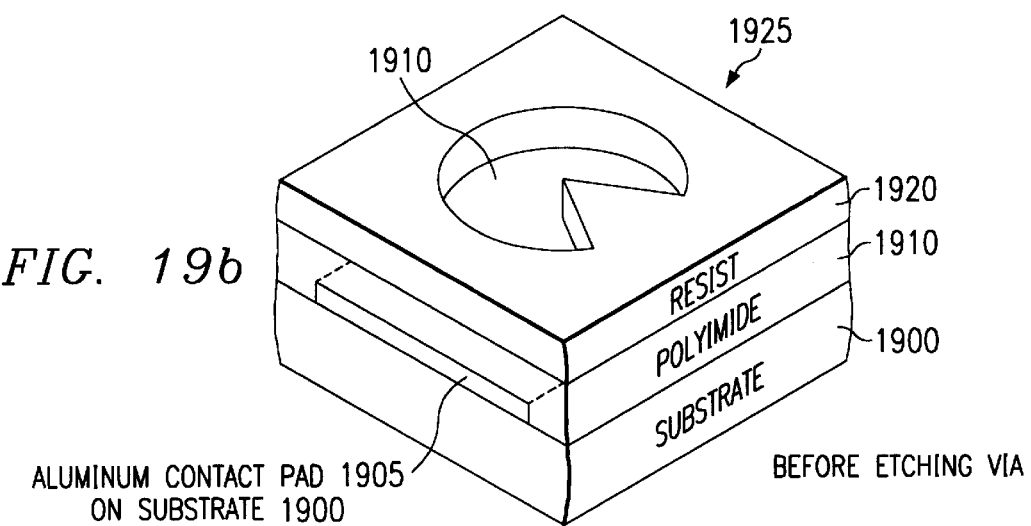
Figure 19C:
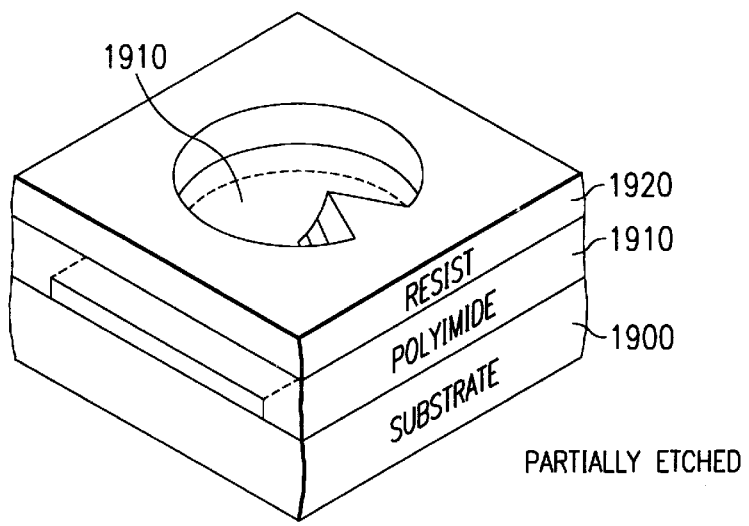
Figure 19D:
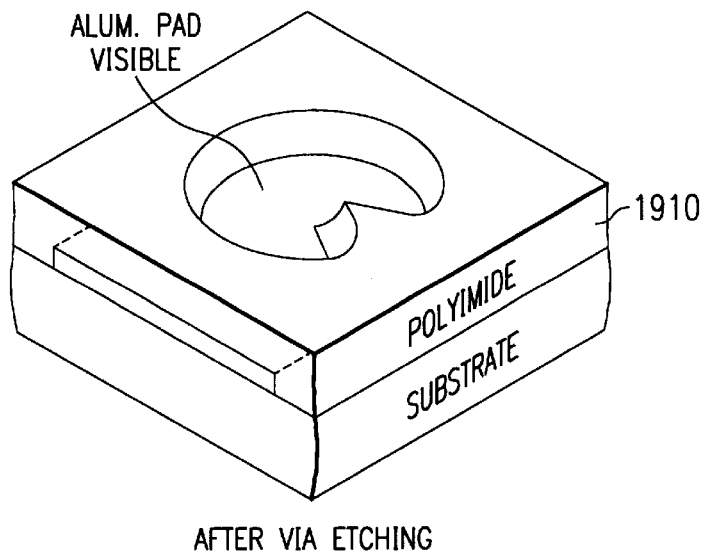
Figure 19E:
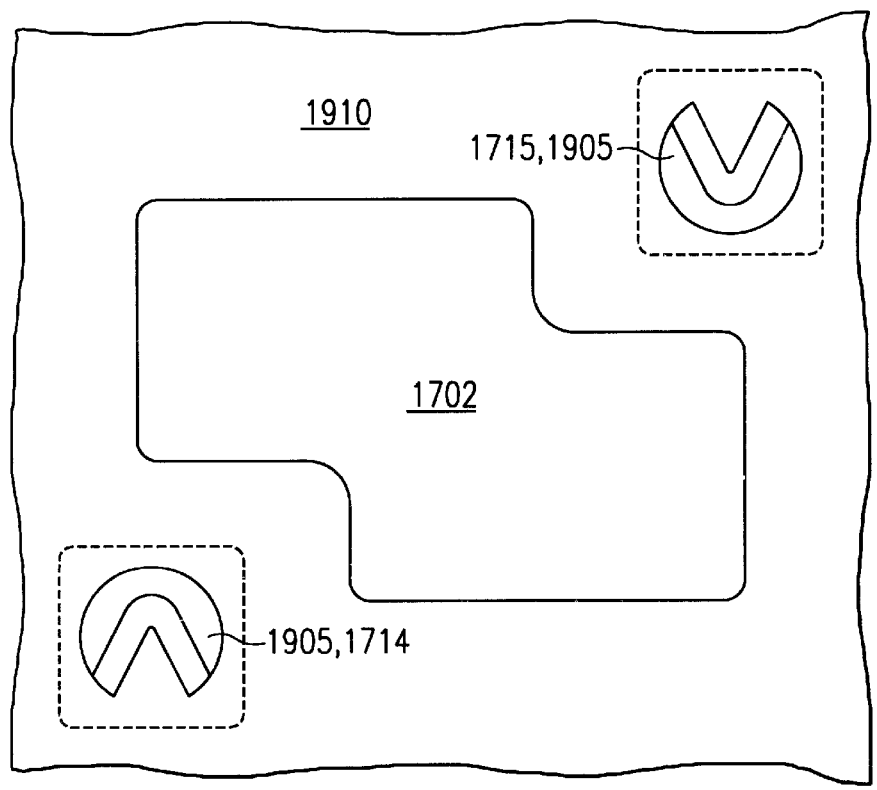

FIGS. 19a–d illustrate steps of a preferred embodiment method of fabrication of the ramped feet of bolometer 1700. In particular, start with aluminum contact pads 1714–1715 plus any other desired circuitry such as correlated doubled sampler circuitry on substrate 1710; pads 1714–1715 may connect laterally or vertically through vias to such circuitry. Next, spin on a 2 mm thick layer 1910 of sacrificial polyimide over substrate 1900 plus aluminum pads 1905 and any other exposed circuitry. The polyimide thickness equals the desired spacing of the suspended bolometer over the substrate. Next, deposit a 25 nm layer of nitride and a 14 nm layer of titanium absorber; follow this with photolithography and etching to pattern the titanium plus nitride to form absorber 1702 on polyimide 1910. Then spin on and pattern photoresist 1920 with a circle-missing-a-wedge shaped vias 1925 as illustrated in plan and perspective views in FIGS. 19a–b; these vias are at corners of absorber 1702. Etch polyimide 1910 and photoresist 1920 simultaneously in a low pressure oxygen reactive ion etch system. As the polyimide surface erodes, the wedge point in the photoresist is also etched on the sides and becomes shorter and narrower, progressively exposing more of the top surface of the polyimide wedge point; see FIG. 19c. Continue etching the polyimide until exposing underlying aluminum pad 1905. The result is a sloped-wall wedge point via which may be easily coated with chemical vapor deposited or sputtered or evaporated material; see perspective view FIG. 19d showing a single via and plan view FIG. 19e showing the location of the vias relative to absorber 1702.

Next, deposit a second 50 nm layer of nitride (which electrically isolates the titanium) followed by a 100–200 nm layer of amorphous silicon by plasma enhanced chemical vapor deposition (PECVD) with in situ doping by $PF_5$ or $BCl_3$ followed by a 20 nm layer of nitride; this set of three layers will form the ramped feet, the support arms, and the temperature dependent resistor. Control the nitride deposition conditions so that the stack of nitride, titanium, nitride, polysilicon, and top nitride passivation layer will be relaxed with minimal differential stress so that the absorber 1702 plus resistor 1704 structure will not curl due to different stresses in the layers. Indeed, plasma enhanced deposition of nitride conditions can be adjusted to yield anywhere from $2\times10^9$ dynes/$cm^2$ compressive to $5\times10^9$ dynes/$cm^2$ tensile stress. Thus use a low stress (e.g., less than $1\times10^9$ dynes/$cm^2$) nitride for the bottom layer, next sputter titanium which typically is tensile but the layer is very thin; deposit the middle nitride again with low stress; deposit the amorphous silicon; and lastly deposit the top nitride with low stress and with a thickness to insure the flatness of the stack of layers after removal of the polyimide. Further, the nitride overall coating deters chemical attack and moisture invasion for long term stability of the resistance.

Then spin on photoresist and pattern it to define the temperature variable resistor, the support arms, and the ramped feet, and anisotropically etch the amorphous silicon plus nitride with the pattern photoresist as etch mask to form the resistor, support arms, and ramped feet. This leaves a portion of pad 1714–1715 exposed; see FIG. 19f.

Spin on photoresist and pattern it to define the thin metal electrical conductors along the support arms and down the ramped feet to the aluminum pads 1714–1715; then deposit a 10–20 nm thick layer of metal, such as aluminum, Ni or Ti and liftoff the photoresist to form the metal conductors. Next, spinon photoresist and photolithographically pattern it to define metal links connecting the aluminum pads 1714–1715 to the top of the ramped feet, then deposit 1000 nm of aluminum, liftoff the photoresist to form the links. Lastly, remove the polyimide with an oxygen plasma to leave the completed bolometer detector suspended over the substrate.

Superpixel bolometer array preferred embodiment

Figure 20:
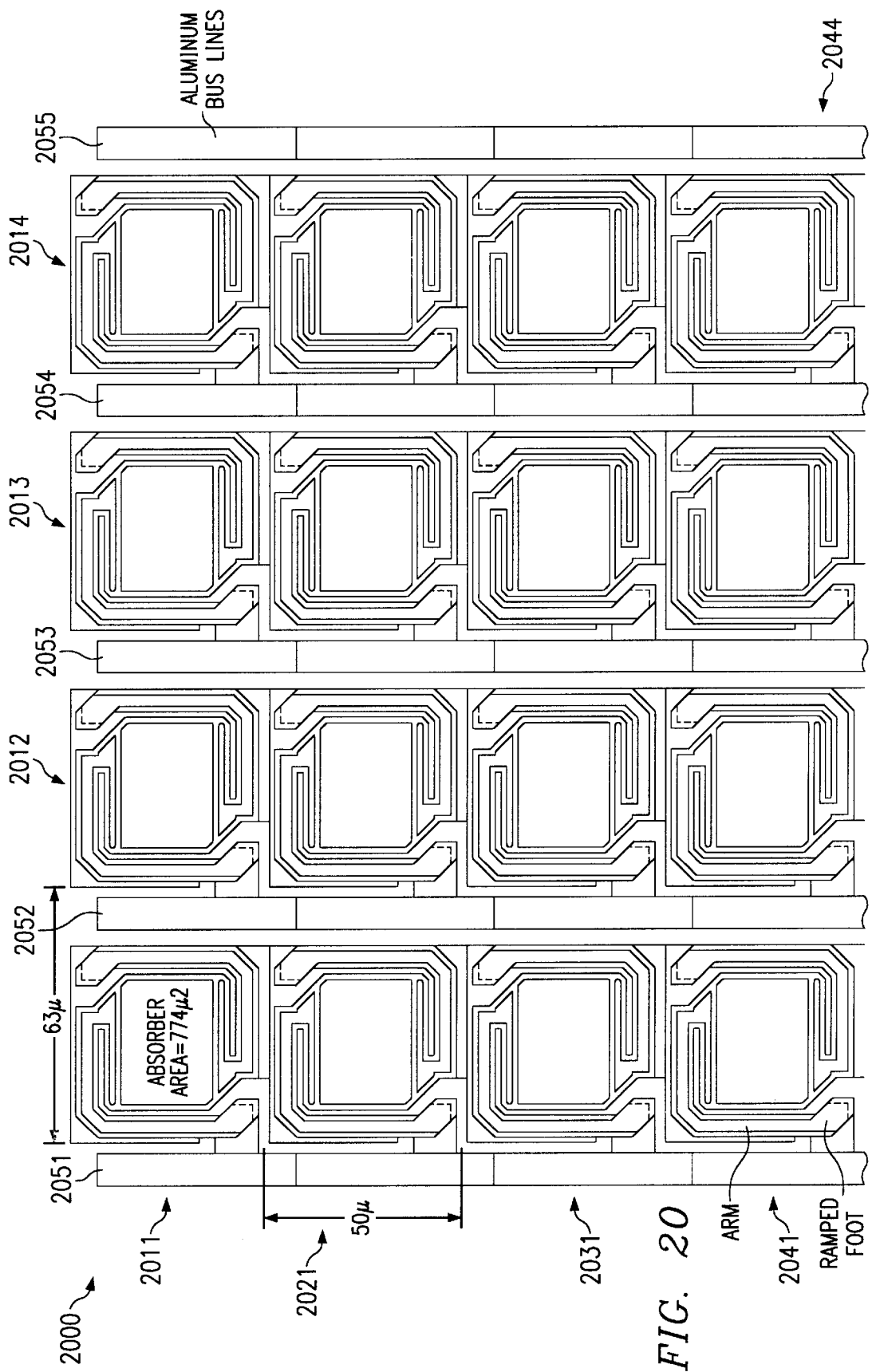
FIG. 20 is a plan view of a preferred embodiment array of pixels.

FIG. 20 illustrates in plan view four-by-four preferred embodiment array 2000 of roughly square bolometers 2011–2044 with each bolometer similar to bolometer 1800 and suspended over the substrate with ramped feet connecting to pads which connect to metal bus lines 2051–2055. Each bolometer has an absorber area of about 35 μm by 35 μm in a total area (including metal bus lines 2051–2055) of 50 μm by 63 μm. Metal bus lines 2051–2055 connect all bolometers 2011–2044 in parallel (lines 2051, 2053, and 2055 form one detector connection and lines 2052 and 2054 form the other detector connection) to form a single detector (superpixel) with large area but without a single large suspended area which has attendant mechanical problems. Indeed, if one or more of bolometers 2011–2044 fails, such as by support arm breakage, the remaining fifteen bolometers still may function and provide sufficient detector performance. Further, the parallel arrangement of N smaller bolometers gives a signal-to-noise ratio improvement by a factor of $\sqrt{N}$ over a single bolometer.

In particular, at low modulation frequencies (chopping) of the input radiation the sensitivity of a single bolometer is a direct function of the thermal resistance of the support arms and the radiation absorbing area. For modulation frequencies $f_c$ bolometer sensitivity includes another factor proportional to $\tanh(1/f_c RC)$ where R is the thermal resistance of the support arms and C is the thermal capacity (thermal mass) of the suspended material, which includes the absorber. Typical values would be roughly as follows: $f_c$ about 30 Hz, R about $2\times10^7$ deg-sec/joule-m, and C about $10^{-9}$ joule/deg. Thus with modulation an increase in absorber area to increase sensitivity has a countervailing decrease in the tanh factor due to the increase in thermal mass C. Further, increasing thermal resistance R to increase sensitivity likewise has a countervailing decrease in the tanh factor from the increase in R. Thus an array of bolometers in parallel allows for increased absorbing area without change in the thermal mass or thermal resistance of an individual bolometer.

An alternative connects the bolometers in a row (column) of an array in series and the rows (columns) in parallel or the bolometers in a columns (row) in parallel and the parallel columns (rows) then connected in series. This has the advantage of simple connections; for example, in FIG. 20 the lefthand metal line 2051 and the righthand metal line 2055 would be the two connections for the bolometer radiation absorbing resistance.

Spiral support arm superpixel bolometer array preferred embodiment

Figure 21A:
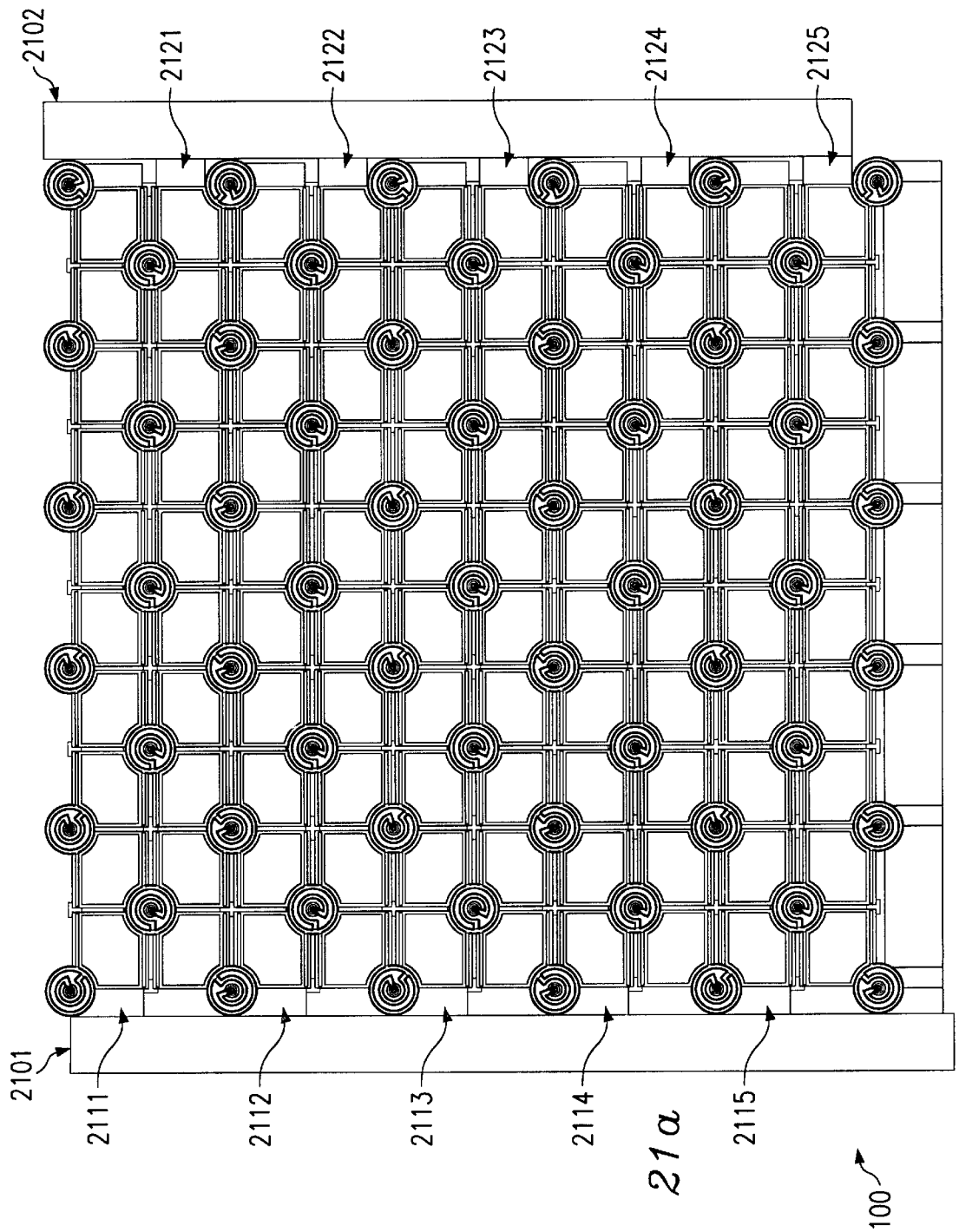
Figure 21B:
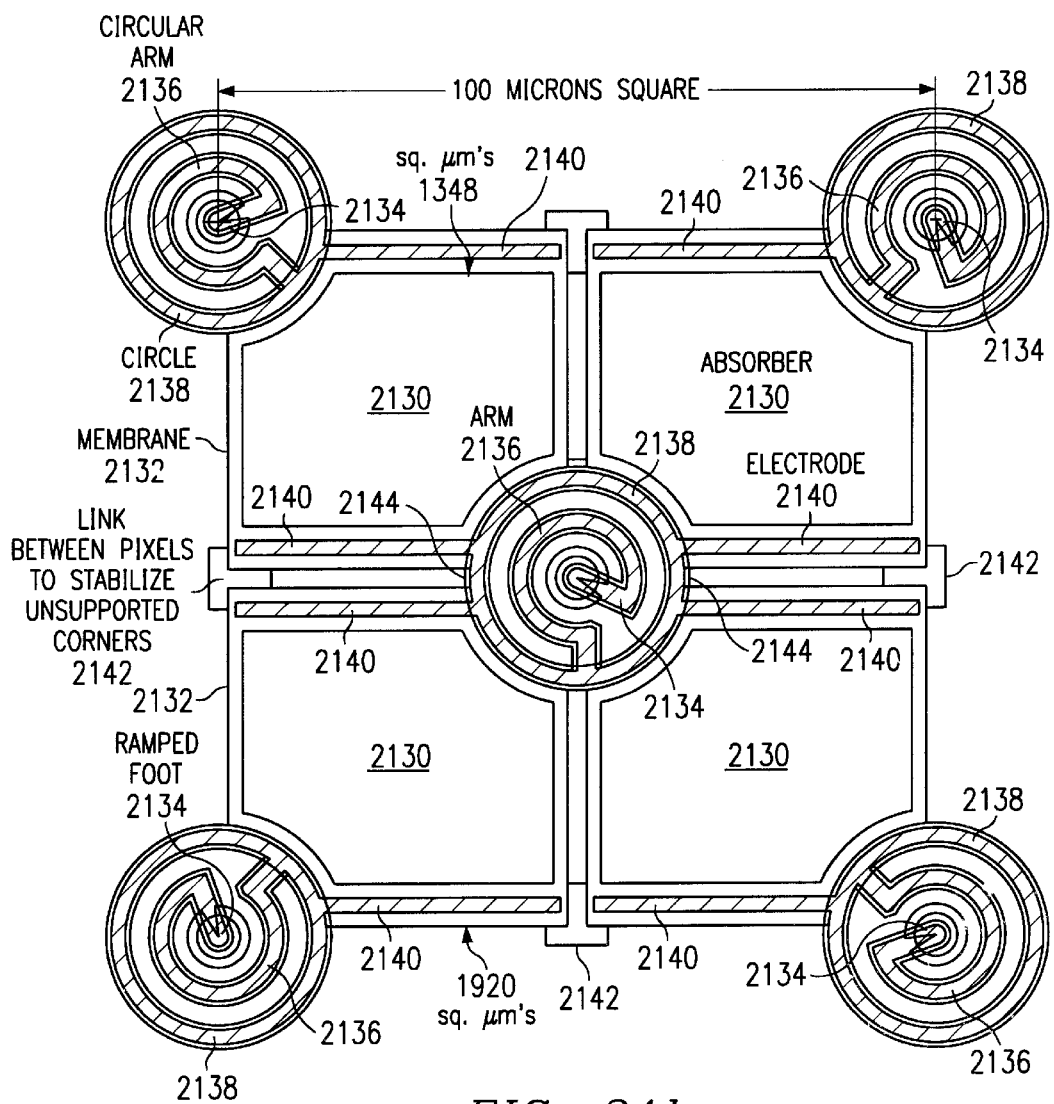
Figure 21C:
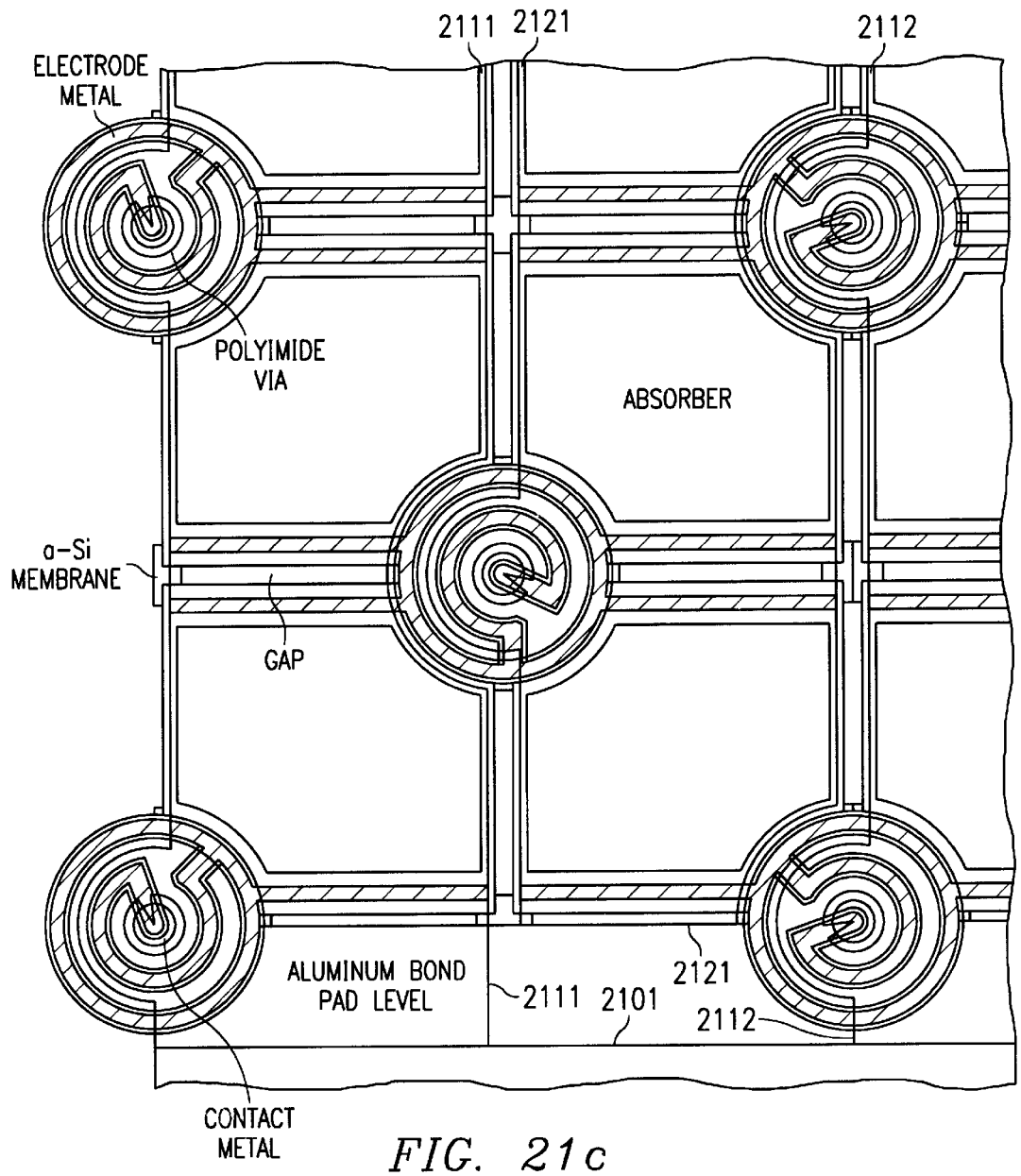

FIG. 21a illustrates in plan view preferred embodiment ten-by-ten array 2100 of roughly square bolometers with each bolometer suspended over the substrate by annular support arms with ramped feet connecting to pads which connect to metal lines 2111–2115 or 2121–2125 with bus 2101 tying lines 2111–2115 together and bus 2102 tying lines 2121–2125 together. FIGS. 21b–c show bolometer details in an expanded view of a two-by-two subarray of array 2100. Each bolometer has an absorber 2130 area of about 1348 μm² on a suspended membrane 2132 (made, for example, of a stack of nitride/amorphous silicon/nitride) of total area of about 1920 μm². Ramped feet 2134 connect to annular support arms 2136 with each annular support arm about 50 μm long and about 4 mm wide; annular support arms 2136 each has a thin metal strip for electrical connection and provides the thermal resistance analogous to support arms 1806–1807 of bolometer 1800. The top metal level (aluminum, nickel, titanium or similar metal, about 10 nm thick and 3 μm wide) extends up a ramped foot 2134 onto an annular support arm 2136 to annulus 2138 along the edges of four adjacent bolometer membranes 2132 to form an electrode 2140 along an edge of each of the four adjacent membranes plus membrane connectors 2144 which are portions of an annulus 2138; see FIGS. 21b–c. Membrane links 2142 connect the corners of four adjacent bolometer membranes which do not connect to an annulus 2138; this provides mechanical support to help avoid curling of the membranes. As with bolometers 1700 and 1800, the bolometer membranes 2132 are made of nitride/amorphous silicon/nitride.

FIG. 21c illustrates the bottom level metal lines 2111 and 2112 on which the ramped feet in the four corners of the Figure connect and metal line 2121 on which the ramped foot in the center of the Figure connects.

Support arms 2136 extend a little more than three quarters of a complete annulus in the plane of membrane 2132. To increase thermal resistivity to the underlying substrate, support arms 2136 could be made longer by using a spiral shape so more than a full turn in the plane of membrane 2132 can be realized.

Stress tolerant superpixel bolometer array preferred embodiment

Figure 19F:
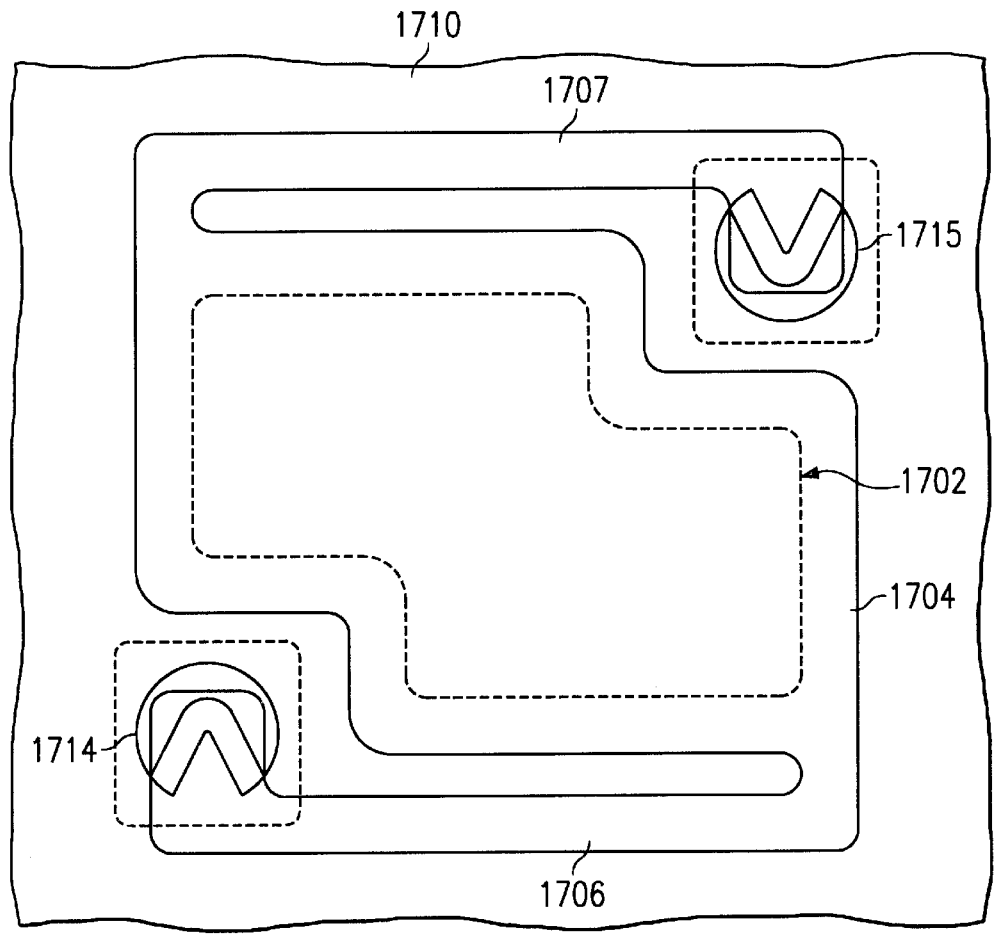

The low stress approach to bolometer fabrication described in connection with FIGS. 19e–f requires process control to avoid suspended membrane curling which could cause the membranes of superpixel 2100 to touch the substrate (loss of thermal isolation), either in the centers or at the array perimeter as illustrated in cross sectional elevation views in FIGS. 21d–e, respectively. FIG. 21f shows stress tolerant preferred embodiment superpixel 2170 which adds a perimeter of dummy pixels 2171 and uses deposition conditions centered about parameter values which would give a slightly upward curling membrane. The perimeter dummy pixels 2171 may make contact with the substrate as in FIG. 21f, but active pixels 2173 remain thermally isolated from the substrate. For a ten-by-ten active array, superpixel 2170 has a twelve-by-twelve array of pixels with only the inner ten-by-ten subarray pixels being active. This perimeter of dummy pixels thus permits a wider range of deposition parameters which yield working superpixels because the chance of downward curling is minimize and upward curling does not disrupt the superpixel.

Figure 21G:
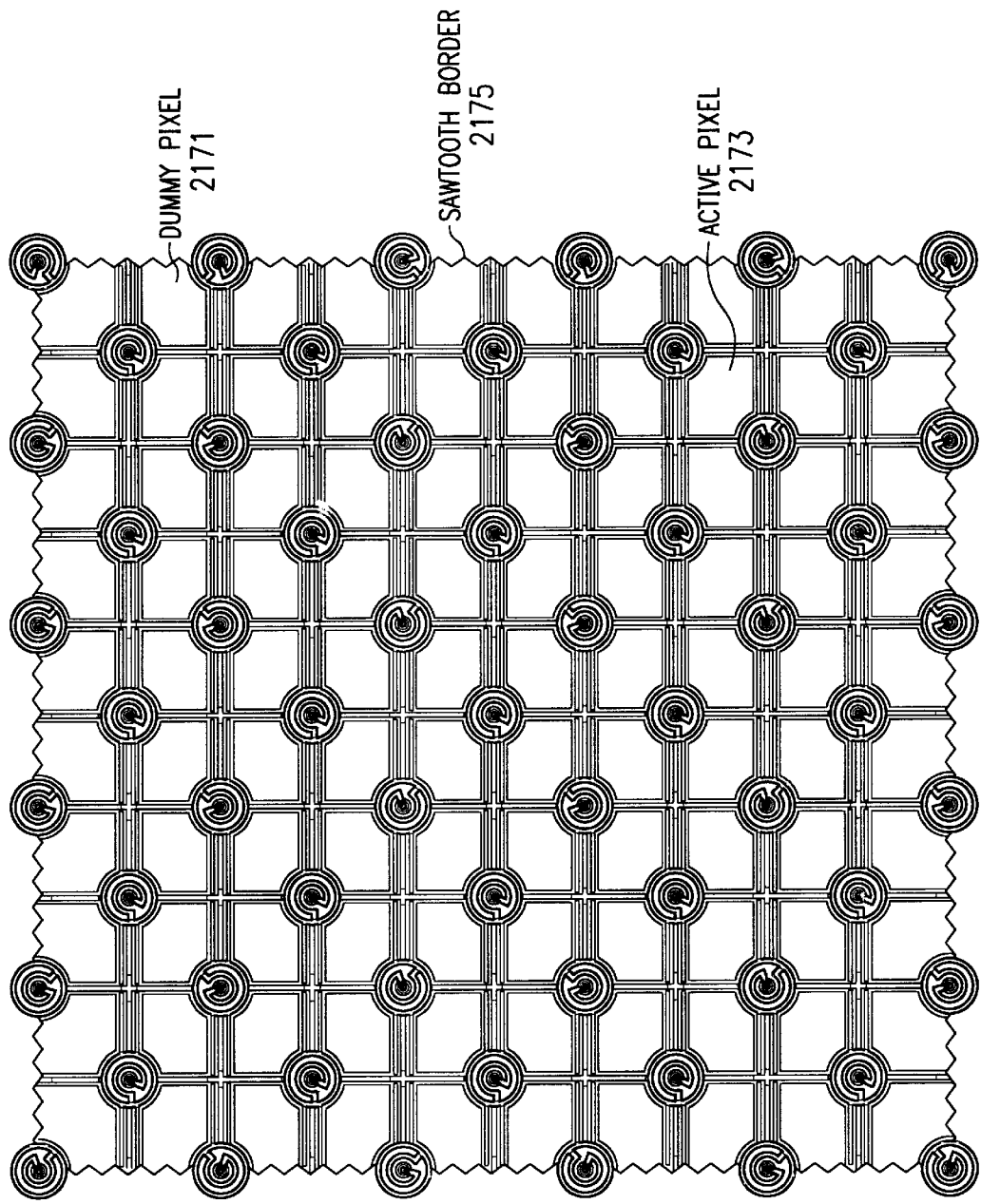

Further, a sawtooth border may be added to the outside edges of the perimeter dummy pixels to lessen their thermal contact with the substrate. See plan view FIG. 21g illustrating a central ten-by-ten active pixel 2173 array and a perimeter of dummy pixels 2171. The sawtooth edge 2175 has been shown with large teeth for clarity although only a small teeth would also provide additional thermal isolation.

Hidden support arm bolometer array preferred embodiment

Figure 22C:
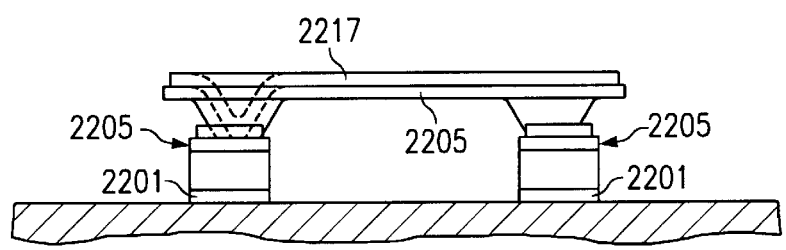
Figure 22B:
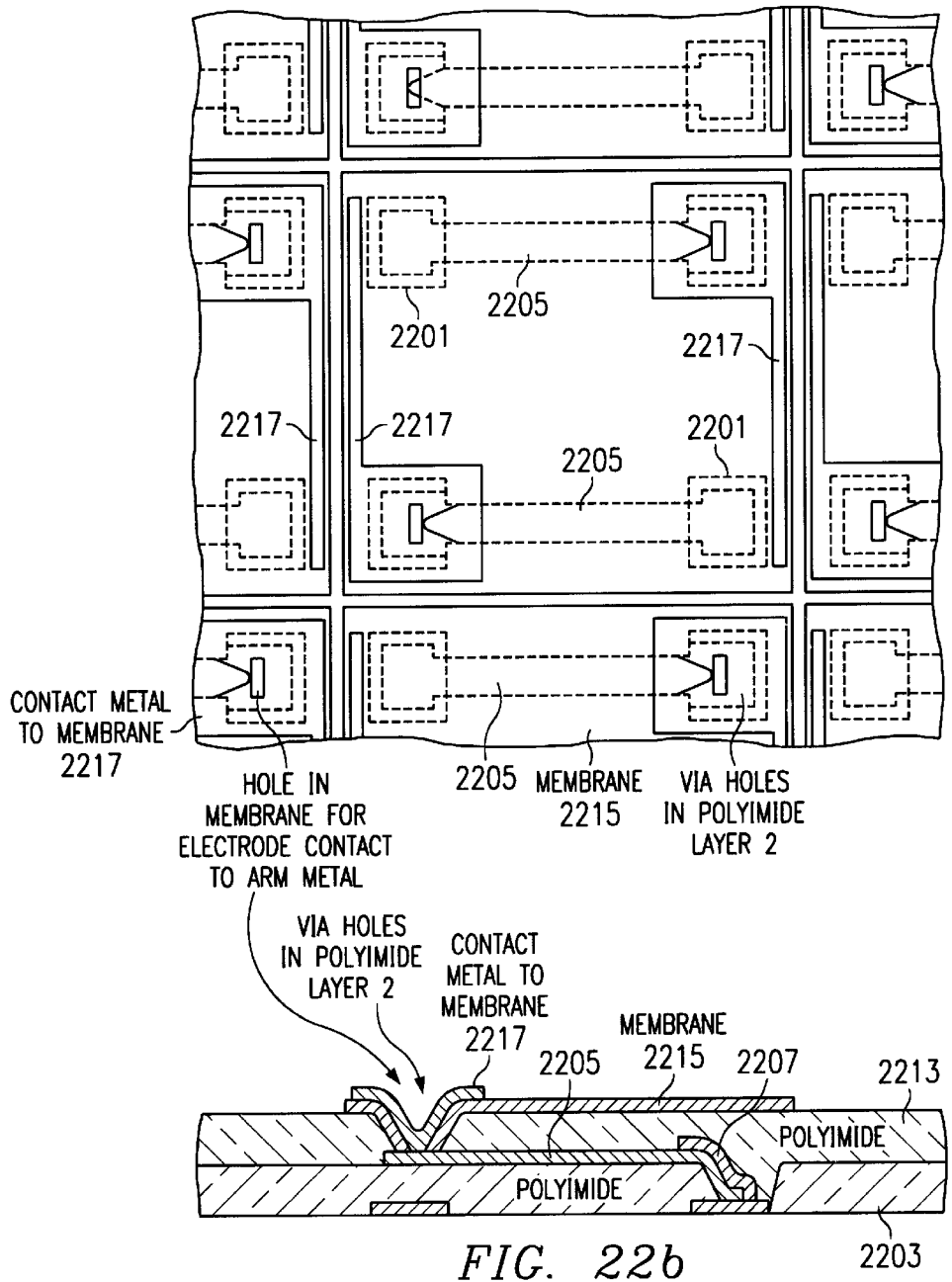

FIGS. 22a–d show steps for fabrication of a preferred embodiment high fill factor bolometer array which basically has the support arms under the suspended absorber and resistor. This permits minimum spacing between adjacent bolometers as would be required when the bolometer array is used for imaging or high resolution spectrometer purposes and each bolometer could be a separately sensed pixel. Of course, this high fill factor array could also be used as a superpixel with the columns of pads 2201 connected together analogous to those of FIGS. 20–21 and used in chemical sensors. The individual bolometers shown in plan view in FIG. 22b are square, but other tiling shapes could be used such as rectangles and hexagons. The bolometers may have any convenient size, such as 50 m, with a spacing between adjacent bolometers as small as 1 $\mu$m wide to allow for plasma removal of the supporting materials used during fabrication. Indeed, the spacing between adjacent bolometers is less than the width of a support arm.

The preferred embodiment method of fabrication includes steps and materials previously described in connection with FIGS. 19a–d and proceeds as follows:

(1) Deposit first polyimide layer 2203 (about 1 $\mu$m thick) on a substrate with circuitry already formed and connecting to metal landing pads 2201 on which bolometer support arms will be formed. Landing pads 2201 are spaced according to the desired pixel size. Form vias (use wedge shaped photoresist and a oxygen plasma etching of polyimide as previously described in connection with FIGS. 19a–d ) through first polyimide 2203 layer down to the metal landing pads 2201; see FIG. 22a which shows a plan view in the lefthad portion and a corresponding cross sectional view in the righthand portion.

(2) Deposit layers of support arm material and electrical conductor material (which may be the same or different, for example, amorphous silicon and metal) with the layers conformally extending down the vias to landing pads 2201. Photolithographically pattern and etch the layers to form the support arms; the support arm material may be patterned and etched prior to the conductor material deposition which then is patterned and etched. This forms support arms 2205 which may be 4 $\mu$m wide and 200–400 nm thick. To insure electrical connection from the electrical conductor material to landing pads 2201, support arms 2205 do not cover all of landing pads 2201, and metal foot contact tab 2207 is formed by deposition and photolithographic patterning and etching. See FIG. 22a. Alternatively, with separate patterning and etching of the support arm material and the electrical conductor material, the electrical conductor material may directly connect to landing pads 2201 (analogous to the aluminum deposited on the amorphous silicon support arm in FIG. 17b).

(3) Deposit second polyimide layer 2213 (about 1 $\mu$m thick) on the support arms 2205 and first polyimide layer 2203; second polyimide layer 2213 fills in the vias in first polyimide layer 2203 and has a planar surface. Form the absorbers on polyimide 2213 by deposition of layers of nitride and titanium followed by photolithography and etching as previously described. The absorber will be in the center portion of the bolometer analogous to absorber 1892 in FIG. 18; the absorber and resistor may occupy 80–90% of the bolometer area depending upon bolometer size.

(4) Form vias through second polyimide layer 2213 down to the ends of support arms 2205 which are remote from landing pads 2201; see FIG. 22b which shows a plan view in the lefthand portion and a corresponding cross sectional view in the righthand portion. Again, wedge shaped vias could be used. Next, deposit layers of nitride and amorphous silicon which will be the resistor material. The stacking of nitride, titanium, nitride, amorphous silicon, and (eventual) top nitride forms the bolometer membrane 2215. As previously described in the Low Stress section, the nitride can be deposited in a low stress state and the thickness of the top nitride used to suppress curling of the individual bolometers.

(5) Photolithographically pattern and etch membrane 2215 to form separate pixels and also to open holes in membrane 2215 at the bottoms of the vias in second polyimide layer 2213 to expose portions of the ends of support arms 2205. To make electrical connection from the resistor material to support arms 2205 metal and to extend along one side of the resistor as in FIG. 18, contact metal 2217 is formed by photolithographic patterning, metal deposition, and resist liftoff. In the same manner, thick metal links may be formed to connect the thin metal 2217 across the ramped foot to support arm metal 2205. See FIG. 22b.

Figure 22D:
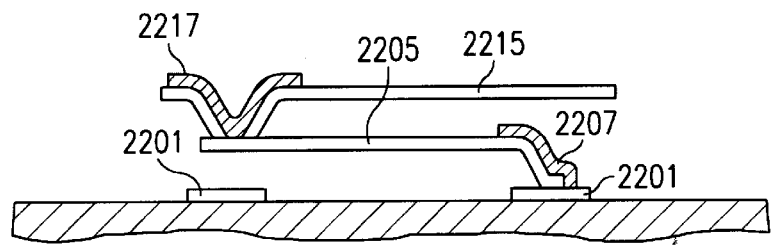

(6) Deposit the top nitride layer and patterned to separate the pixels and then remove both polyimide layers to complete the suspended bolometer, see FIG. 22c–d which are cross sectional elevation views from perpendicular directions.

Substrate reference resistor preferred embodiment

Figure 10A:
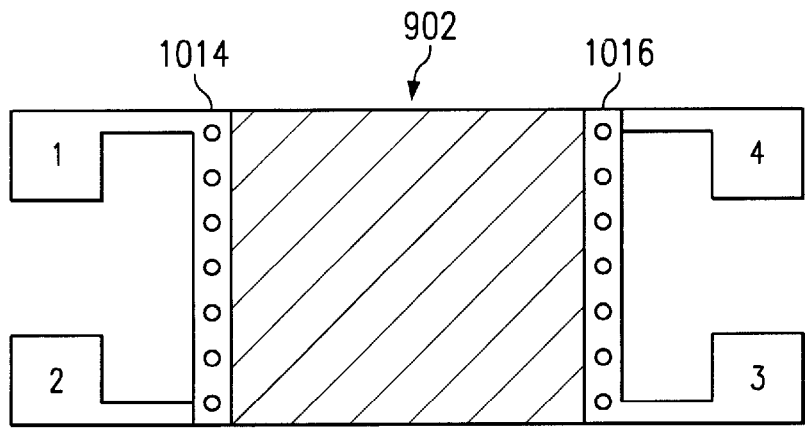
FIGS. 10a–b are plan and cross sectional elevation views of a pixel of the other preferred embodiment.
Figure 10B:
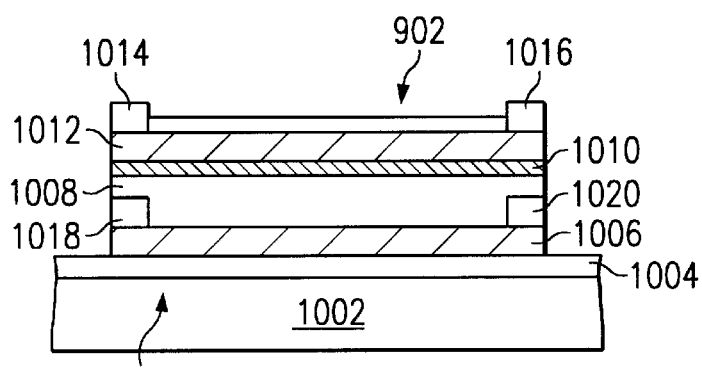
Figure 23A:
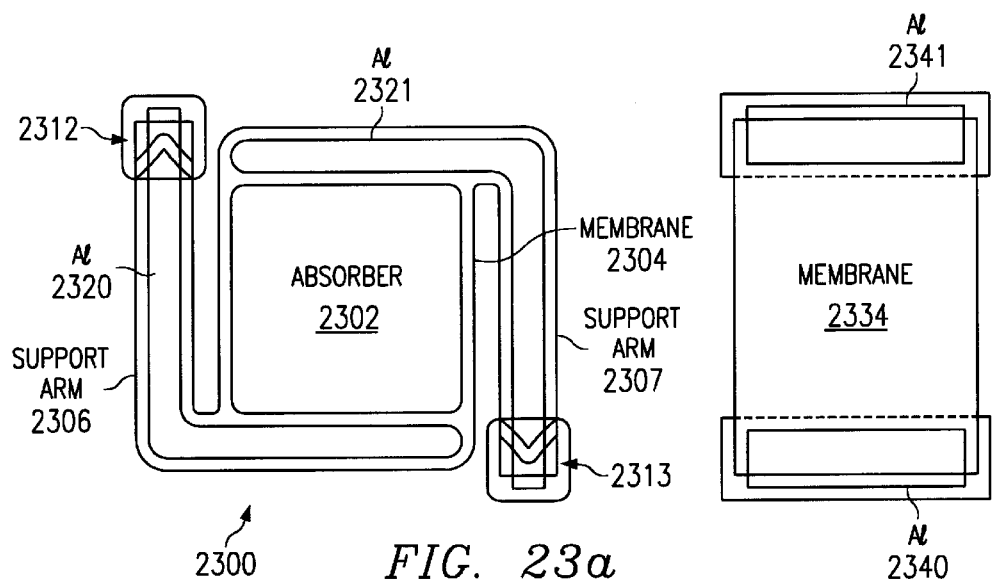
FIGS. 23a–e illustrate a preferred embodiment suspended bolometer with substrate resistor.

FIGS. 10a–b illustrate the photoconductor version of detector 900 of FIG. 9a with both photoconductors 902–904 essentially thermally coupled to the substrate and photoconductor 904 shielded from input radiation by photoconductor 902. The bolometer version of detector 900 is more involved because bolometer 902 needs to be upended over the substrate for thermal isolation and shielding a likewise suspended bolometer 904 is not as simple as with photoconductors. Preferred embodiment bolometer detector 2300 avoids the problem by the use of an unshielded reference resistor 904 located on the substrate and made of the same resistive material as the suspended bolometer; e.g., made of amorphous silicon. See FIG. 23a showing in plan view support arms 2306–2307 with ramped feet 2312–2313 suspending nitride/amorphous silicon/nitride membrane 2304 over the underlying substrate with absorber 2302 on the suspended membrane and adjacent reference resistor made of membrane nitride/amorphous silicon/nitride 2334 directly on the substrate. Metal films 2320–2321 lower electrical resistance along support arms 2306–2307 and make edge contact to the suspended amorphous silicon resistor of membrane 2304 and similarly aluminum films 2340–2341 make edge contact to the amorphous silicon resistor of membrane 2334.

Alternative embodiments for reference resistor 904: resistor may be placed under the detector to conserve area. This would be a great advantage in an array of pixels used for image detection in which ideally the pixels should have as little non-active space between them as possible. Such a substrate reference resistor need not be shielded because it is thermally coupled to the substrate which acts as a heat reservoir. Indeed, such reference resistor 2334 provides compensation for drift in substrate temperature because the substrate temperature is also the equilibrium bolometer temperature without input radiation. Thus with the bolometer resistor and the substrate reference resistor being of the same material and resistance (size), a change in the substrate temperature leads to the same change in the two resistances and cancels out.

Figure 23B:
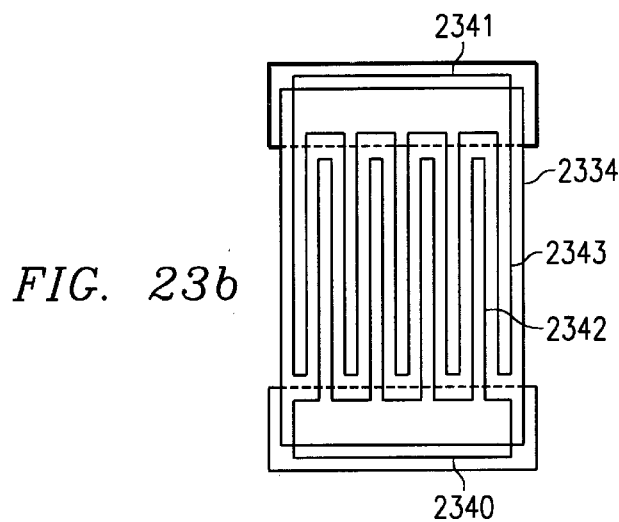

For a superpixel array bolometer, the substrate reference resistor may have a proportionately smaller resistance, and smaller resistance can be achieved by a shorter membrane 2334 or by extending aluminum films 2340–2341 into fingers or a combination. See FIG. 23b showing fingers 2342–2343. For a single pixel bolometer resistance of 20 megohms and a ten-by-ten parallel-connected array of bolometers forming a superpixel, the substrate reference resistor resistance would be only 200 kiloohms to match the resistance of the one hundred bolometers in parallel in the superpixel. The resistance of the membrane may be adjusted by adjusting the doping level. Resistances in the range of 1 kiloohm to 500 megohms may be desired, depending upon the readout circuitry.

The thermally-coupled-to-substrate reference resistor 2334 with metal contacts 2340–2341 could also be located directly below the suspended bolometer element 2304. This would allow for maximum utilization of available die area and is applicable to both superpixel and single elements comprising an area or linear array. FIG. 23e shows the cross sectional view of suspended membrane 2350 and associated support arm 2353 directly above and isolated from reference resistor member 2355. The same insulator material 2352 used for electrical isolation of absorber 2351 could be used so as to allow for a reflector metal 2357 to be applied to the top surface of membrane 2355. While not required for all applications, two of the electrodes can be combined to form a common electrode 2354 resulting in additional optimization of die area. The equivalent schematic diagram is shown to implement a voltage divider network with the suspended element 2358 connected by the common element 2359 to the lower thermal reference resistor 2360.

Figure 23C:
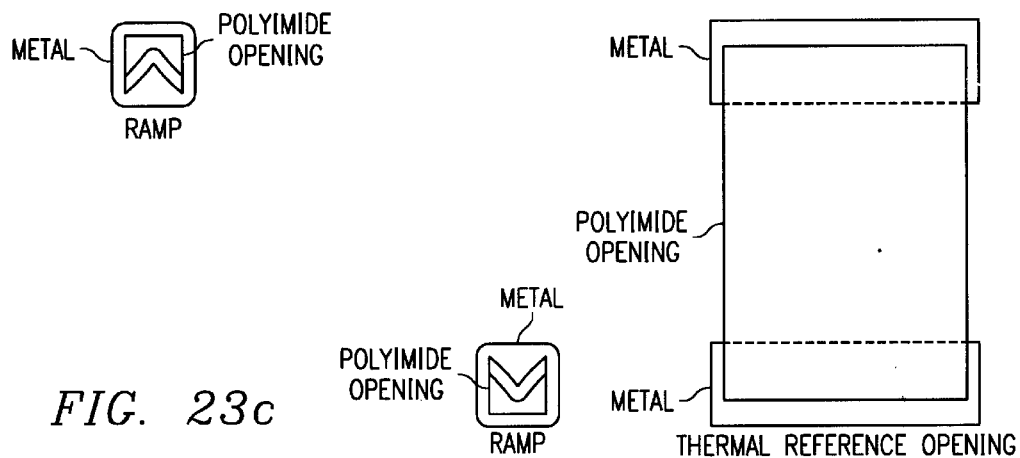
Figure 23D:
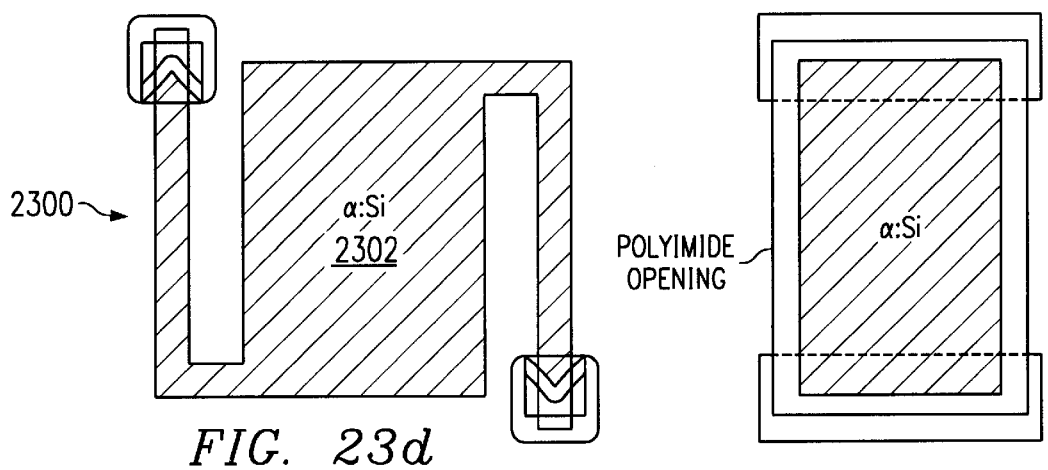
Figure 23E:
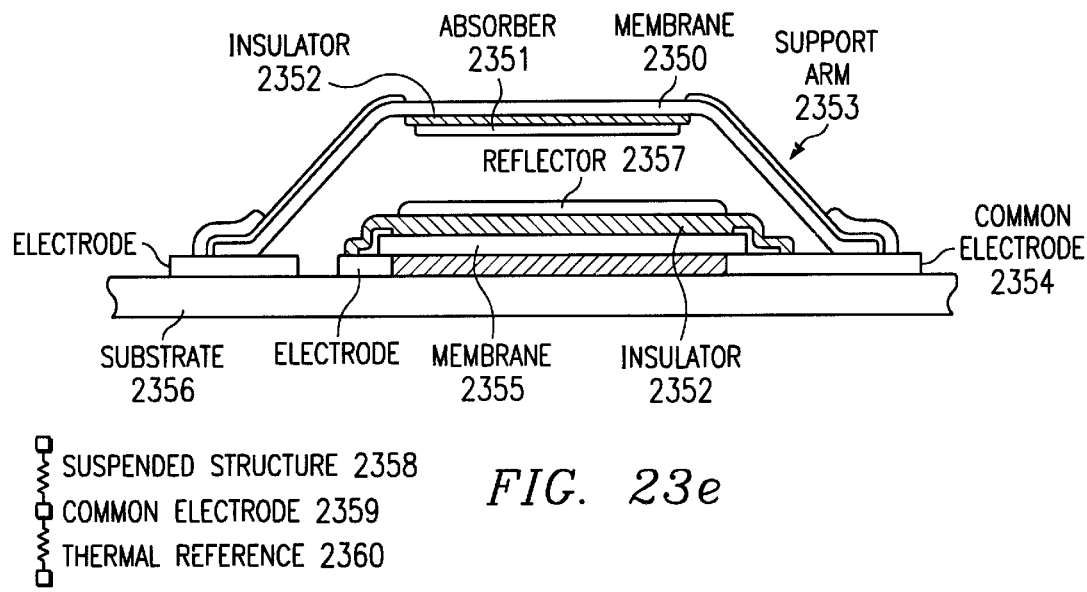

FIGS. 23c–d illustrate steps in fabrication of detector 2300 which follow the steps described in connection with FIGS. 19a–f. First a polyimide layer is formed over the circuitry and metal landing pads and metal reference resistor terminals. Then pattern photoresist with openings for the ramped feet (again with a wedge shape) and the location of the substrate reference resistor; see FIG. 23c. As previously described, plasma etch to erode photoresist and remove polyimide to expose portions of the metal landing pads and resistor terminal. Then deposit nitride, amorphous silicon and nitride and photolithographically pattern it as shown in FIG. 23d. Then ion mill through the nitride to expose amorphous silicon and deposit aluminum, and liftoff, the resist and lastly remove the polyimide as before.

Internal shade package preferred embodiment

Figure 24B:
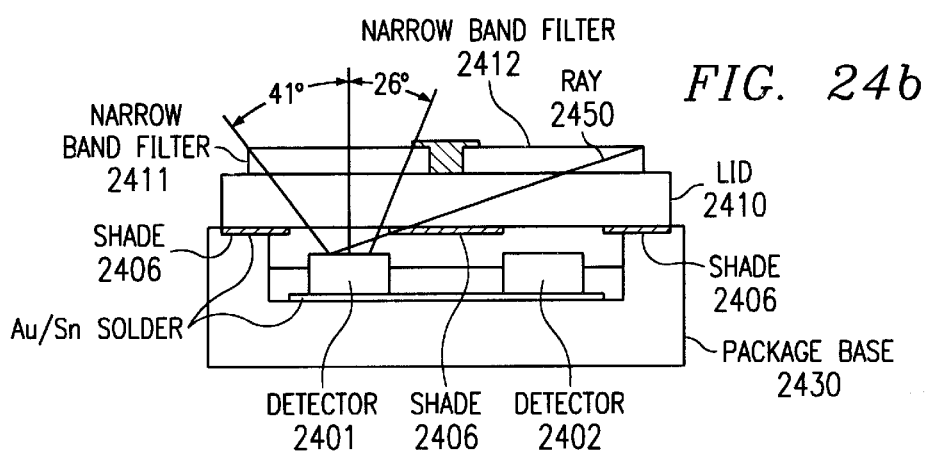
FIGS. 24a–g are plan and cross sectional elevation views of preferred embodiment packaged bolometer detectors and assembly method.
Figure 24A:
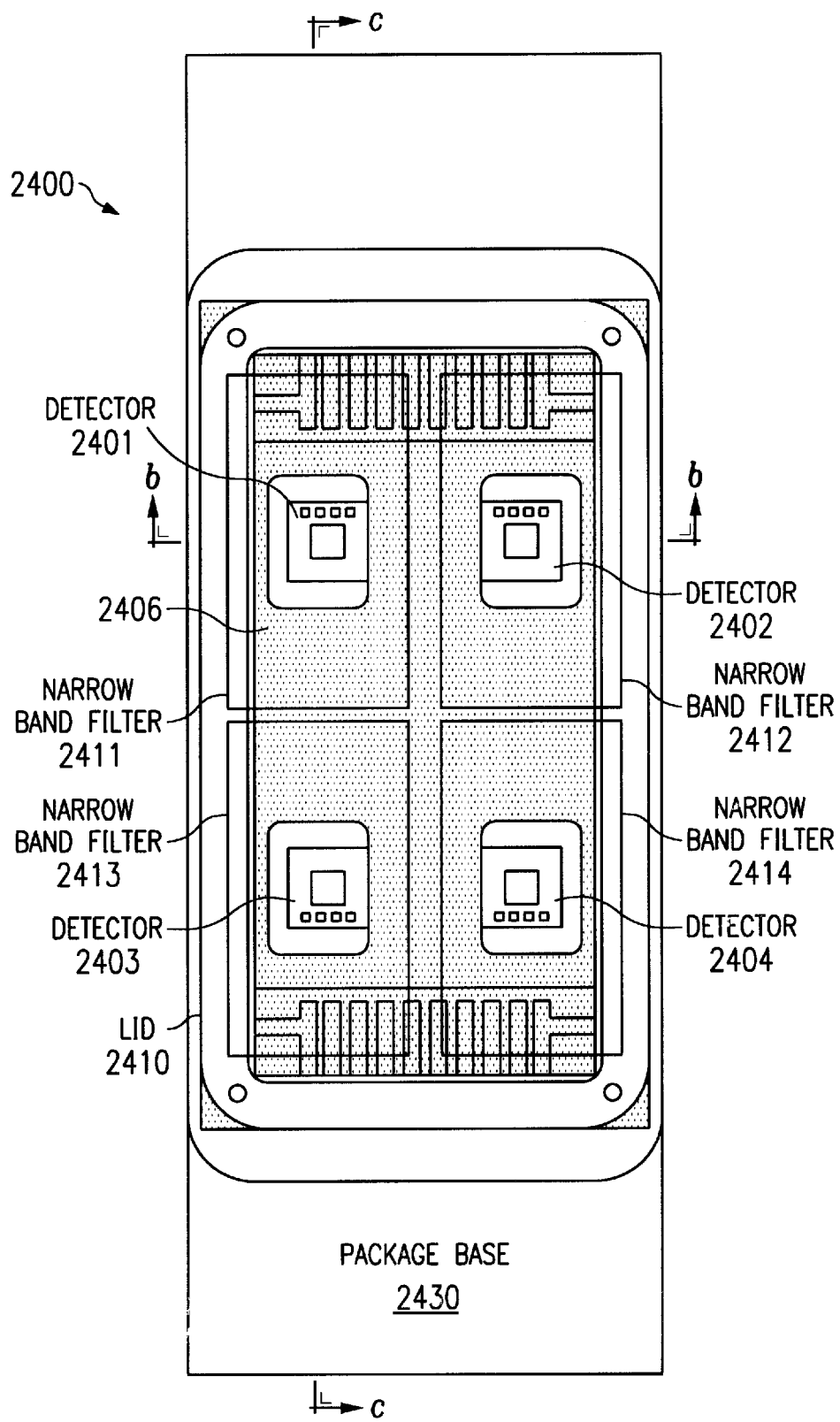
Figure 24C:
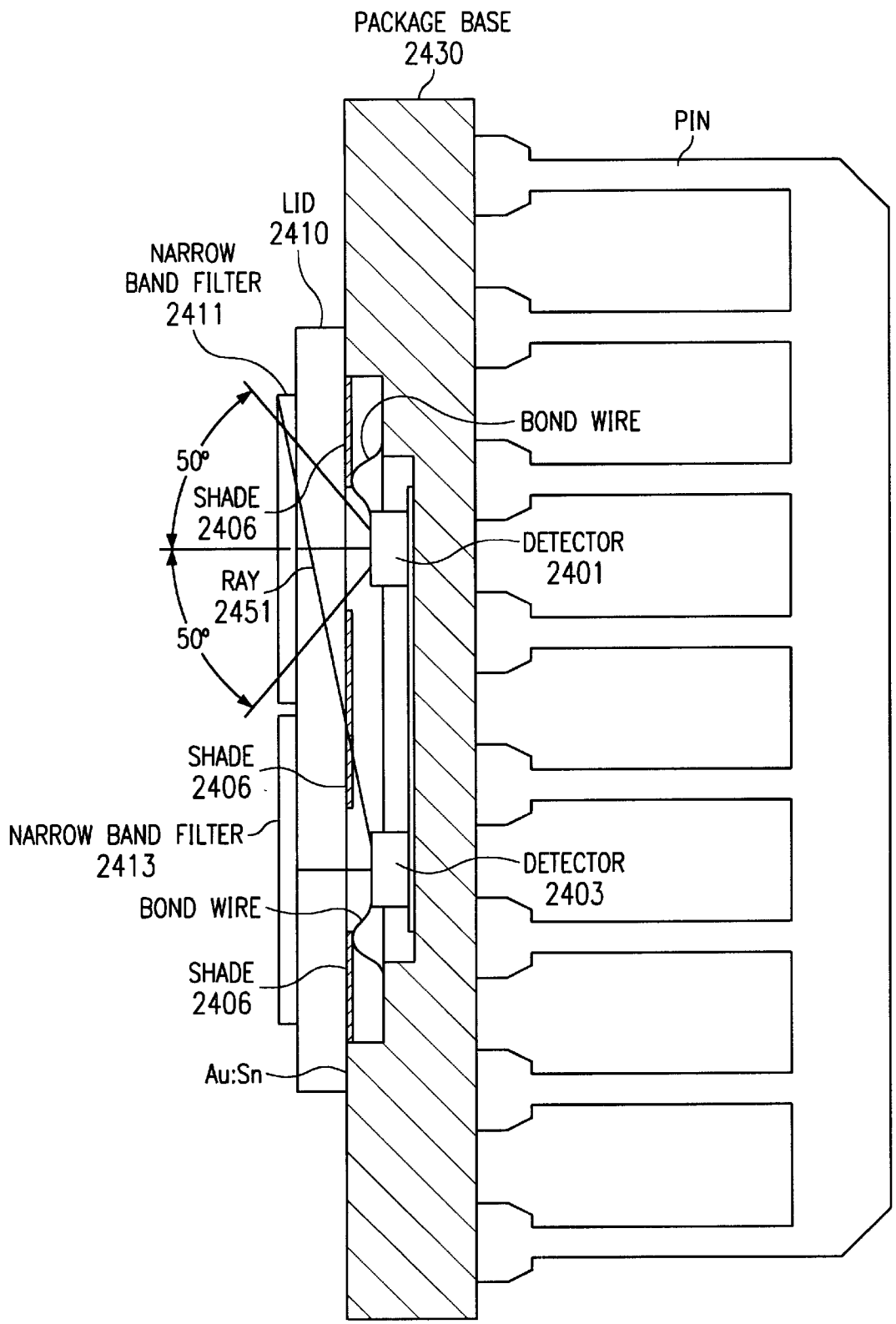

FIGS. 24a–b illustrate in plan and cross sectional elevation views preferred embodiment 2400 vacuum packaged 2 by 2 array of infrared detectors 2401–2404 with an infrared blocking film (shade) 2406 on the inside of infrared transparent package lid 2410. Narrow band optical filters 2411–2414 on lid 2410 are located over corresponding detectors 2401–2404 and openings in shade 2406. As shown in FIG. 24b–c shade 2406 blocks all incident infrared radiation from a detector except that passing through the corresponding overlying filter. The purpose of aperture is to confine off (vertical) axis light to the detector beneath it and to prevent light from being internally reflected in the package from striking a different detector. Internal shade (as opposed to an external shade) is closer to the detectors and thus confines the light to the intended detectors. Indeed, the openings in shade 2406 essentially interpolate the size difference between the detector (small) active area and the optical filter (large) area as indicated by the ray tracings in FIGS. 24b–c. FIG. 24b shows detector 2401 receives radiation incident in a cone with opening angles of 26° and 41° from the perpendicular in the horizontal direction of FIG. 24a,. The angles could vary depending on the application. Also, ray 2450 in FIG. 24b illustrates shade 2406 blocking the path between detector 2401 and filter 2412;.

Each detector 2401–2404 is a silicon integrated circuit with a single bolometer or bolometer array plus circuitry and having a size about 1.5 mm square; the corresponding openings in shade 2406 are about 2 mm by 2.5 mm. Adjacent detectors are separated by roughly 5 mm or 10 mm. Lid 2410 is about 9 mm by 17 mm; and ceramic package base 2430 is about 10 mm by 25 mm by 3 mm thick. Ceramic package base 2430 is made of sintered aluminum oxide with a seal band (for the lid attachment) of gold on nickel. Detectors 2401–2404 are gold:tin (80%:20%) soldered to ceramic package base 2430. The bond wires between the detectors and the package leadframe and leads are generally not shown; only the external portions of the leads prior to separation show in FIG. 24c. Lid 2410 is infrared transparent and made of 0.5 mm thick silicon (or germanium) with a germanium (or other) antireflective coating. Shade 2406 is a gold/nickel/chromium stack of thickness about 0.5 $\mu$m. Detectors 2401–2404 are spaced about 0.25 mm from lid 2410. Filters 2411–2414 are multilayer interference filters about 4 mm by 7 mm and 0.25 mm thick and attached to lid 2410 by an epoxy glue along their perimeters.

Vacuum package preferred embodiment

Detectors 2401–2404 employ bolometers with thermal isolation, so significant gas pressure over detectors 2401–2404 limits their sensitivity by providing a thermal conduction path. Indeed, gas pressures within the cavity between lid 2410 and ceramic package base 2430 should be kept to below 200 mTorr, and preferably below 50–100 mTorr. Gold:tin eutectic attaches lid 2410 to ceramic package base 2430 and also attaches detectors 2401–2404 to the package base. The use of gold:tin rather than epoxy for attachment avoids potential outgassing from the organic epoxy into the cavity. The gold/nickel/chromium shade 2406 is made with gold deposition avoiding trapped gas. A titanium/palladium/gold metal system could also be used. The chromium provides adhesion to the silicon lid 2410, and the nickel provides a diffusion barrier between the chromium and the gold. Shade 2406 may be formed by liftoff with the gold/nickel/chromium deposited on patterned photoresist defining the openings over the detectors. Note that the gold/nickel/chromium extends to the lid perimeter and the gold:tin connects the gold/nickel/chromium on the lid to the gold on nickel seal band in the package base. The gold:tin initially has a thickness of about 50–75 µm but is compressed during the sealing; see the following section for a description of a preferred embodiment sealing method.

Figure 24D:
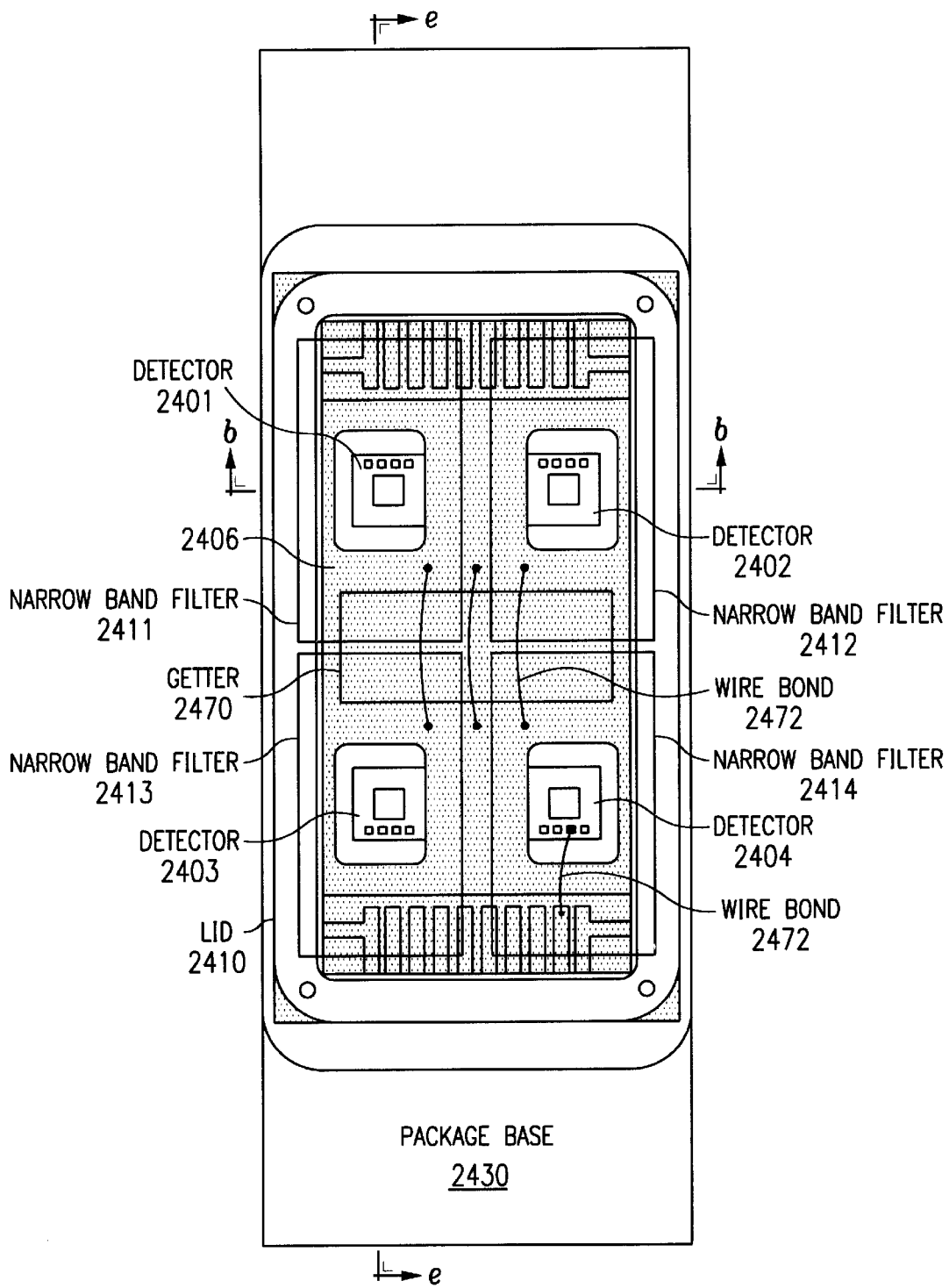

A low temperature getter may be inserted into the cavity and activated; see FIGS. 24c–d illustrating getter 2470 held by wire bonds 2472 attached to the package floor. The getter could also be spot welded or soldered in place. Getter 2470 may be made of zirconium-vanadium-iron or similar gas absorbing materials.

The cavity containing detectors 2401–2404 has a volume of about 80 mm$^3$. Experiments have shown a package 2400 sealed with an initial pressure of about 27 Pa in the cavity has maintained a cavity pressure of less than 40 Pa after a year. In other words, package 2400 has shown a pressure increase of less than 13 Pa over a year, and the same pressure increment should apply for other initial pressures. Package 2400 also has been sealed with an initial pressure of less than 0.133 Pa and accelerated testing has indicated that the pressure would remain less than 1.33 Pa after a year. Thus package 2400 has very low pressure applications.

Package 2400 may be made with different materials and still maintain its vacuum performance. In particular, the lid could be a low porosity, fired ceramic or nonmetallic (poly) crystalline material, or outgassed glasses or VAR metals; and the package base could be made of any of the same materials because all of these materials will have very limited outgassing. An alternative approach would be to use convenient materials but apply a gas diffusion barrier (e.g., silicon nitride) on the cavity surfaces. Indeed, the package base preferably has a gold on nickel coating both as the seal band and on the bottom of the cavity to connect to the gold:tin soldering of the lid and the detectors, respectively. The gold:tin for sealing could be replaced with other low outgas solders or with indium for a low temperature seal.

An alternative package and assembly procedure solders lid 2410 to ceramic package base 2430 without vacuum but provides a port in ceramic package base 2430 so that the cavity can be evacuated after lid attachment. Following evacuation, a low temperature indium solder seal (either melt or cold press) plugs the port. Or the port to the cavity could be a glass tube which may be easily sealed after evacuation by melting.

Alternative versions of the vacuum package could be used for various micromachined and other structures, such as micromechanical resonators, and the lid need not be transparent. The use of gold:tin sealing plus an evaporated or ion plated outer gold layer on the lid will eliminate outgassing found with other lids and maintain the vacuum.

Vacuum package sealing preferred embodiment

Figure 24E:
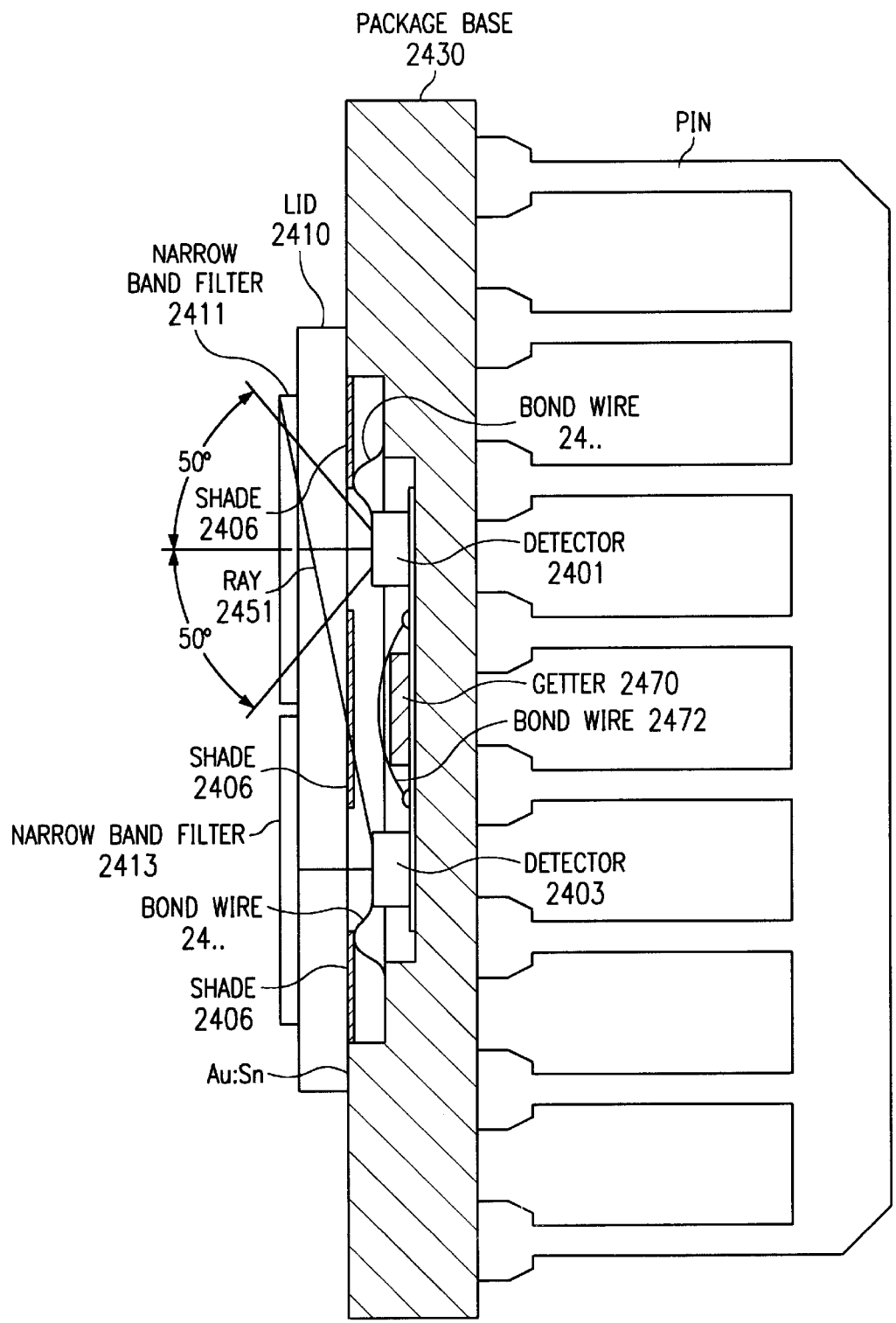
Figure 24F:
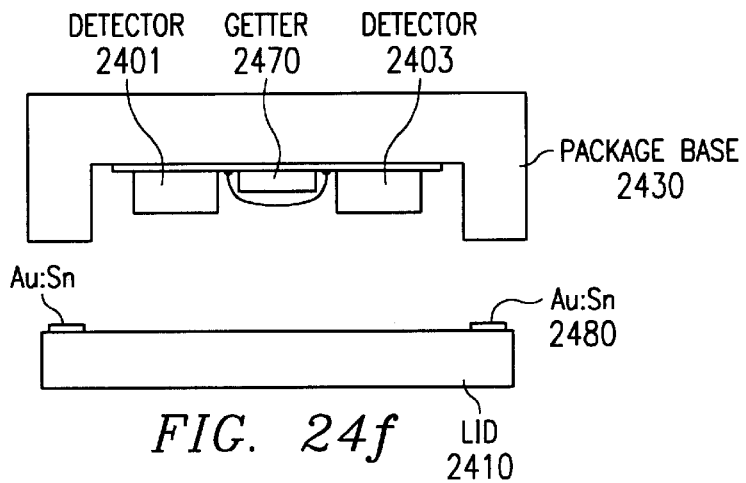
Figure 24G:
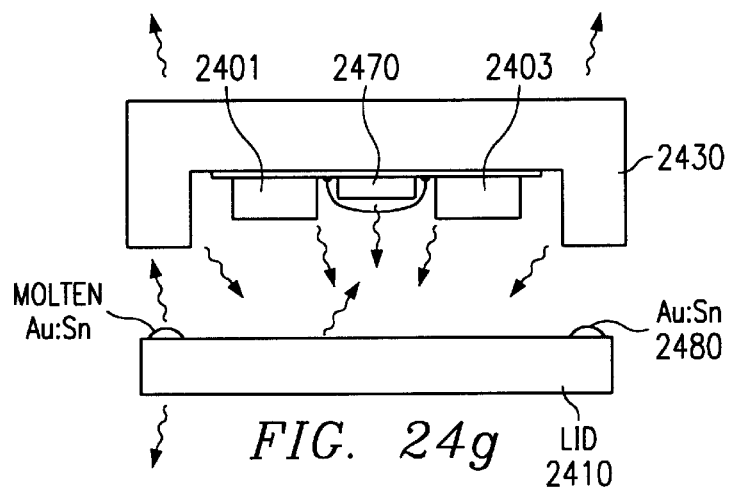
Figure 24H:
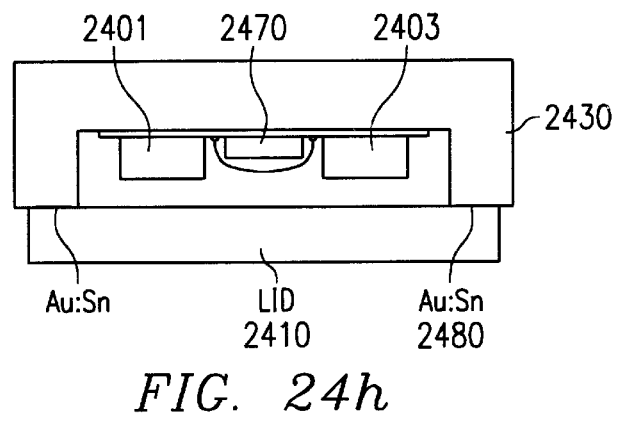

FIGS. 24e–g illustrate a preferred embodiment method of vacuum package 2400 sealing which includes the following steps:

(1) Suspend package base 2430 with attached detectors 2401–2404 and getter 2470 plus gold seal band upside down over lid 2410 with gold:tin perform 2480 tack welded at four corners along the lid perimeter (which has a gold/nickel/chromium surface layer or metals with equivalent function) in a vacuum furnace. Evacuate the furnace down to roughly 0.000133 Pa. See FIG. 24e.

(2) Raise the temperature of the vacuum furnace to 270° C. for 24 hours to bake out and drive off most of the material that would otherwise outgas into the cavity after vacuum sealing. Gold:tin 2480 is a eutectic with a melting point of 280° C. and thus remains in place on lid 2410.

(3) At the end of the bakeout, ramp the temperature up to 310–320° C. and hold it for roughly 6–7 minutes. This melts gold:tin 2480 and allows for further outgassing but does not allow for significant dissolution of gold from the gold/nickel/chromium into the gold:tin and increase the melting point. Having lid 2410 under package base 2430 rather than the opposite orientation prevents the molten gold:tin 2480 from falling off of lid 2410. See FIG. 24f.

(4) Lower package base 2430 onto lid 2410 with molten gold:tin 2480 for a reflow of 2 to 4 minutes to form the seal; see FIG. 24g. Gold:tin 2480 had an initial thickness of about 50–75 µm and compensates for lack of planarity in either the lid or package base or both. Then rapidly cool down to room temperature.

The bakeout also provides getter activation: getter 2470 operates by chemical reaction with surface adsorbed gasses to form nonvolatiles, and thermal activation drives unreacted getter material to the surface for eventual reaction with gasses adsorbed after lid sealing.

Alternatives would be to reverse the orientation with lid 2410 over package base 2430 but have the gold:tin preform on package base 2430. The bakeout time and temperature could be varied, such as 12 or 36 hours. Also, getter 2470 could be electrically activated; this provides more complete activation and thus a shorter bakeout could be tolerated due to the greater gettering capacity. Also, other materials could be used provided the outer layers prevent outgassing. Thus sputtered gold which absorbs argon (the sputtering agent) will not maintain the vacuum, but evaporated gold will maintain vacuum.

Spectrometer

Figure 25A:
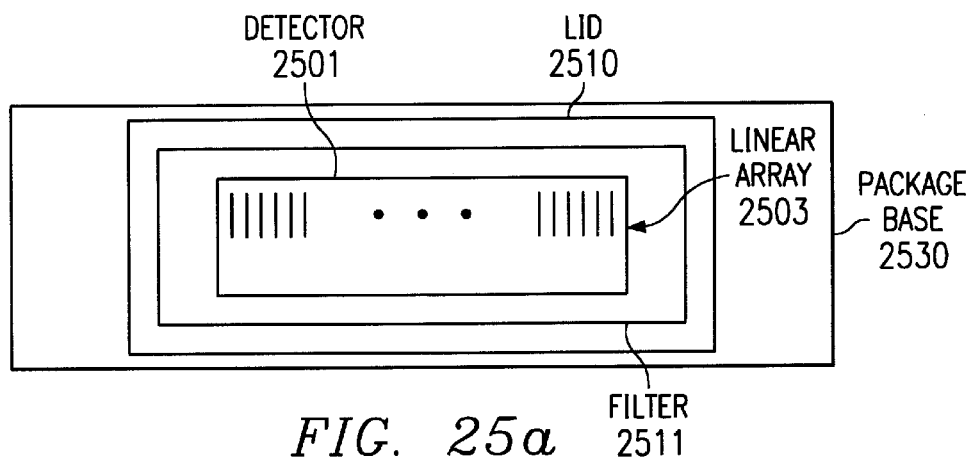
FIGS. 25a–b illustrate preferred embodiment spectrometers.

Characterization of the chemical or physical state of a system can be established by measurement of the infrared absorption or emission from the system over an entire range of wavelengths with a spectrometer. FIG. 25a shows in plan view preferred embodiment spectrometer 2500 as including detector integrated circuit 2501 which includes a linear array 2503 of 128 adjoining 2 by 10 superpixel bolometers in package base 2530 and under infrared transparent lid 2510 with graded interference filter 2511. Filter 2511 has a rectangular shape and is a passband filter with a center wavelength which varies linearly along the direction of the long sides which is also the long direction of linear array 2503 of bolometers. The center wavelength varies by a factor of about 2 over the length of linear array 2503. Thus the band of wavelengths impinging on the bolometers varies along the long direction of linear array 2503 and this provides spectral separation. Of course, somewhat collimated input radiation limits crosstalk and improves resolution; the close proximity of the pixels and continuous nature of the filter precludes the use of a shade.

Figure 25B:
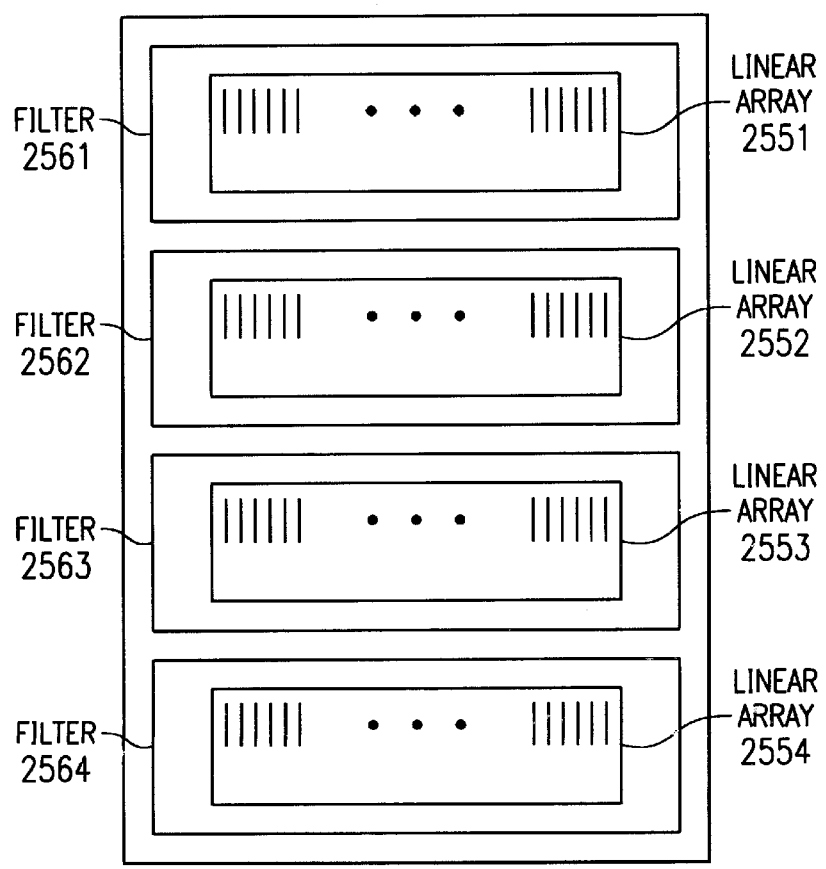

Simply by placing multiple bolometer arrays together, a wider range of wavelengths can be analyzed. FIG. 25b shows four adjacent arrays with array 2551 under filter 2561 which has center wavelengths in the range 2.0 to 4.0 $\mu$m, array 2552 under filter 2562 which has center wavelengths in the range 3.5 to 7.0 $\mu$m, array 2553 under filter 2563 which has center wavelengths in the range 6.0 to 12.0 $\mu$m, and array 2554 under filter 2564 which has center wavelengths in the range of 10.0 to 20.0. Thus the set of four arrays covers the range of 2.0 to 20.0 $\mu$m with a little overlap between arrays and with no single filter center wavelength range exceeding a ratio of 2. The four arrays together roughly separate the spectrum into 400 intervals, so with signal processing the spectrometer may have a resolution of less than 1%.

Figure 26A:
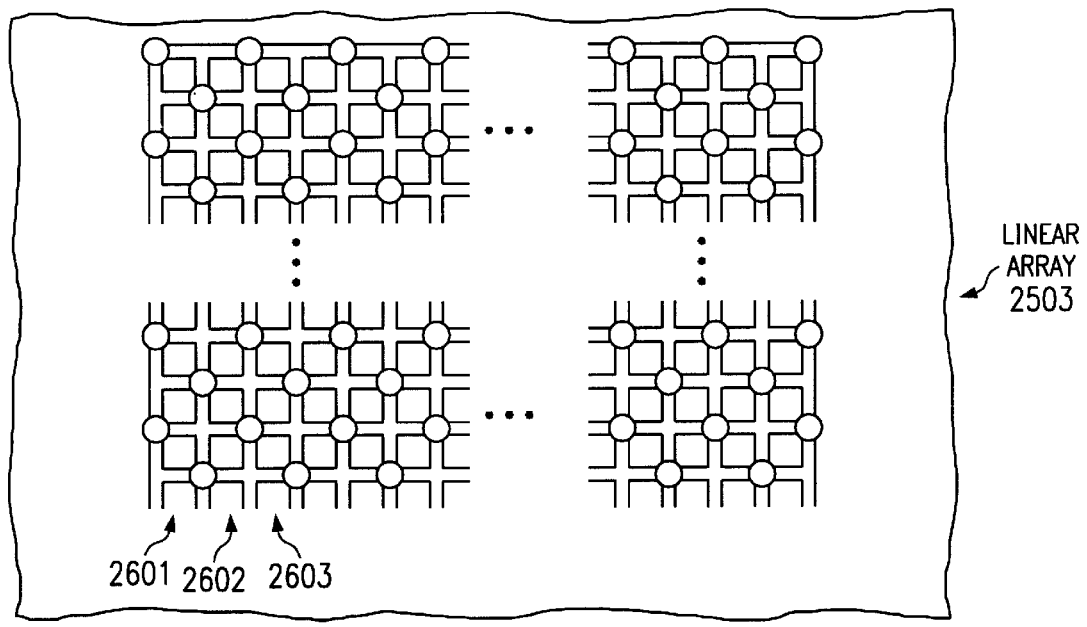
FIGS. 26a–b show aspects of the preferred embodiment spectrometer.
Figure 26B:
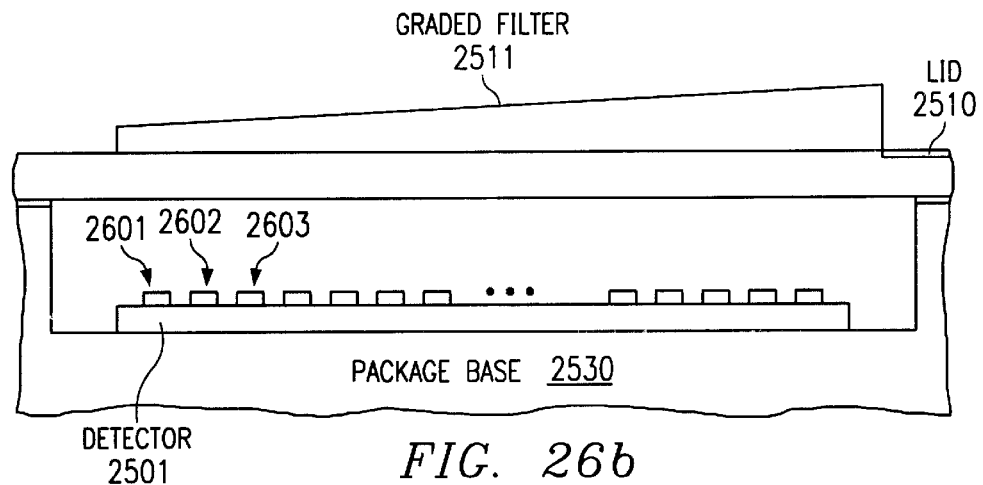

FIGS. 26a–b are plan and cross sectional elevation views of the bolometer area of preferred embodiment spectrometer 2500. Each pixel is about 50 $\mu$m square so the linear array is 12.8 mm long and 0.5 mm wide. Each superpixel would be two columns of ten pixels each, such as columns 2601 and 2602 in FIG. 26a with the readout bus connecting the supports between the two columns; and adjacent superpixels would share a bias voltage source, such as connecting the supports between columns 2602 and 2603. The previously described electronic chopping arrangements and substrate reference resistors may be applied, and the circuitry could be located parallel to the linear array.

Graded interference filter 2511 consists of multiple layers of dielectrics with differing dielectric constants, and the passband center wavelength depends upon the layer thicknesses; the varying of the passband center wavelength follows from varying layer thicknesses. Such filters may be fabricated by graded thickness growths of the dielectric layers, and the number of layers determines the bandwidth of the passband (e.g., a bandwidth of 5–10% of the center wavelength).

Autocalibration

Figure 27:
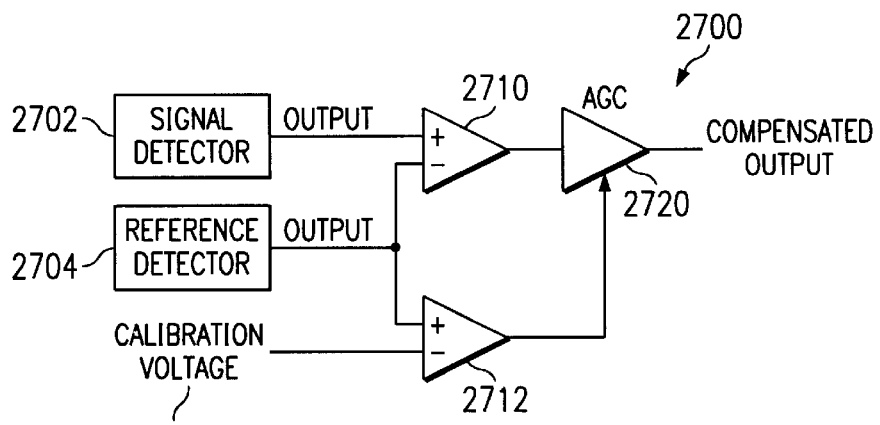
FIG. 27 is a schematic diagram of an autocalibration preferred embodiment.

FIG. 27 schematically shows an autocalibration circuit 2700 for sensor 1400. Circuit 2700 compensates for variations and drift in the output of lamp 1404 without the use of recalibrations which would involve standard gas samples. In particular, the output of one of detectors 1421–1423 would be a "signal detector" output for FIG. 27 and the output of detector 1424 would be the "reference detector" output for FIG. 27. Thus three circuits 2700 would be used: one for each gas detector with all three circuits using the same reference detector. The circuit 2700 operates as follows. The output of signal detector 2702 and the output of reference detector 2704 provide the two inputs to difference amplifier 2710, so the output of amplifier 2710 represents the amount of infrared absorbed by the gas to be measured. If infrared source 1404 were stable, then this is all that would be needed. However, source 1404 may drift, so second difference amplifier 2712 compares the output of reference detector 2704 with a calibration voltage 2706, which may be taken equal to the output of reference detector 2704 at the time of sensor assembly and calibration. Thus the output of amplifier 2712 corresponds to the change in intensity of source 1404, and this output drives automatic gain control circuit 2720 to multiply the output of amplifier 2710 by a factor to restore it to magnitude at the time of sensor assembly and calibration Difference amplifiers 2710–2712 may be constructed from general purpose opamp and the automatic gain control circuit may be constructed as a voltage-controlled resistor in a feedback loop of an opamp connected as in inverting amplifier. Of course, other circuits could be used for the difference amplifier and automatic gain control functions.

Figure 1B:
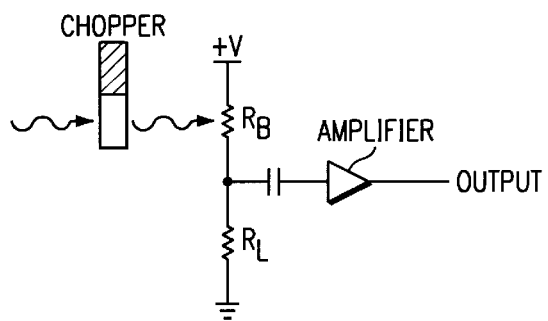
Figure 1C:
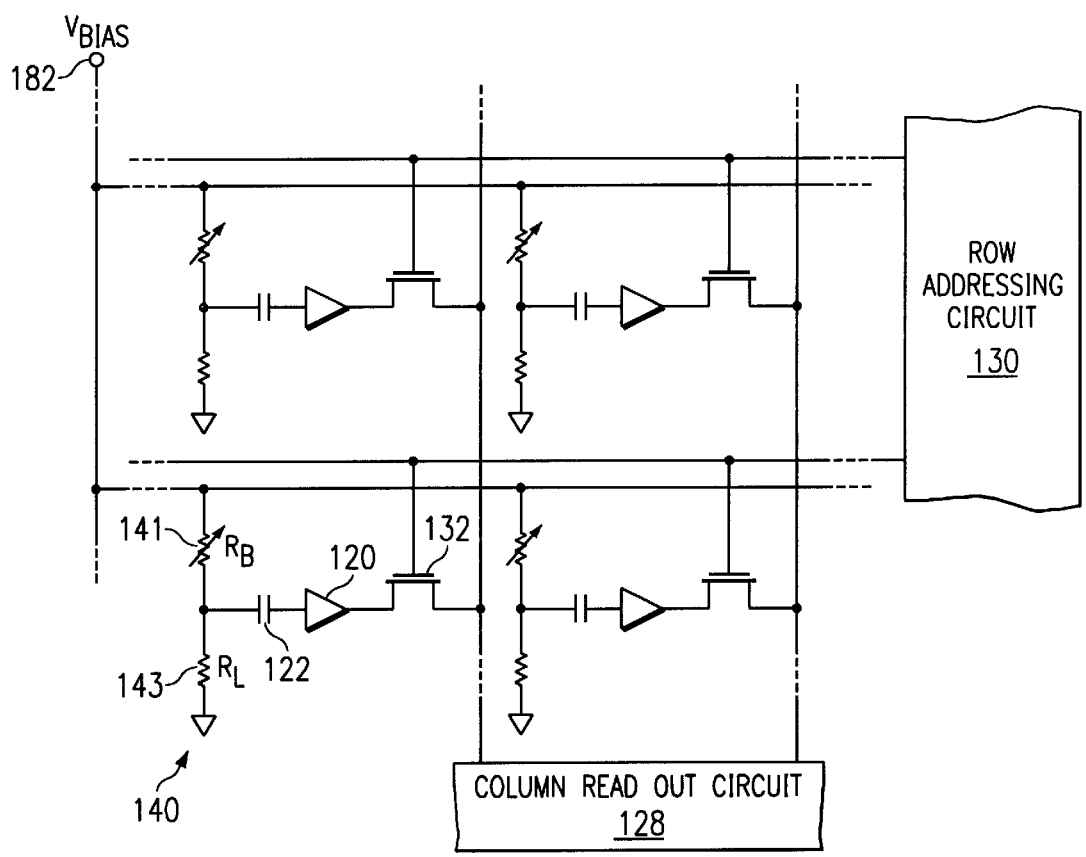

Auto-calibration circuit 2700 could also be used without the electronic chopping: just take signal detectors 2702–2704 to be resistor voltage dividers as in FIG. 1b.

Self-calibration

Figure 28:
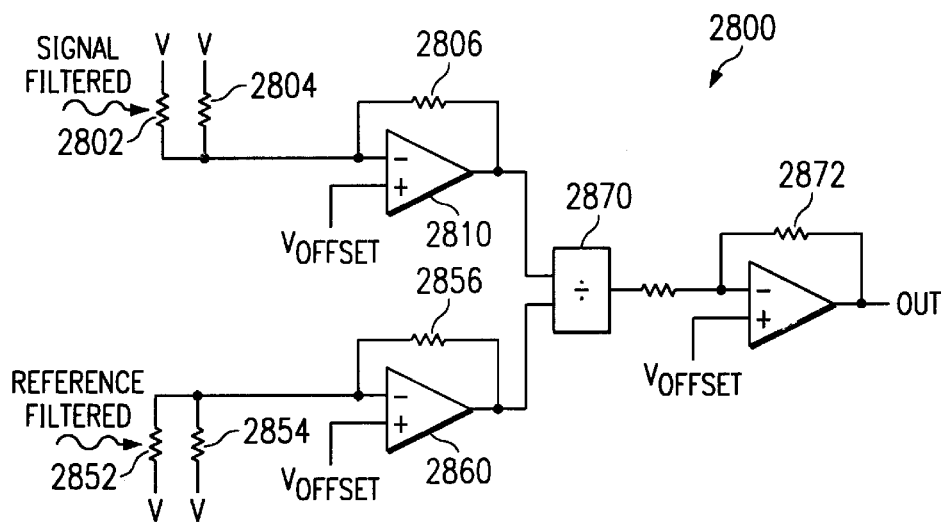
FIG. 28 is a schematic diagram of a self-calibration preferred embodiment.

FIG. 28 illustrates a preferred embodiment readout circuit 2800 with continuous calibration for source intensity plus compensation for ambient temperature in sensors such as sensor 1400 which has both signal detectors and reference detectors. In particular, resistors 2802–2804 correspond to resistors 902–904 of FIG. 9a for a detector of a gas to be measured and resistors 2852–2854 correspond to resistors 902–904 for a reference detector. That is, resistor 2802 receives incident infrared radiation in a narrow band about an absorption line of a gas to be measured and resistor 2804 is shielded from this radiation; and resistor 2852 receives incident infrared radiation in a narrow band away from absorption lines of the gas to be measured and resistor 2854 is also shielded from this radiation. Resistors 2804 and 2854 could also be substrate thermal reference resistors as described in FIG. 23b. Readout circuit 2800 operates as follows.

First, ignore incident radiation. Then resistors 2802 and 2804 with equal resistances and with equal temperature coefficients of resistance implies the current through feedback resistor 2806 is zero and the output of opamp 2810 is zero even as the ambient temperature varies. Similarly, the output of opamp 2860 is zero when resistors 2852 and 2854 have equal resistances and equal temperature coefficients of resistance.

Next, with incident radiation from a source (e.g., infrared source 1404) impinging on resistors 2802 and 2852, the outputs of opamps 2810 and 2860 will reflect the incident radiation flux through the signal and reference filters, respectively. Then the ratio of the two opamp outputs by divider 2870 will be independent of the irradiance of the source and just reflect the signal. More explicitly, let R denote the resistance of resistors 2802, 2804, 2852, and 2854 at a calibration temperature, and let a denote the temperature coefficient of resistance: a change in temperature, DT, yields a change in resistance of aRDT. Presume an ambient temperature change by $DT_A$ and incident radiation additionally changing the temperature of signal resistor 2802 by $DT_S$ and the temperature of reference resistor 2852 by $DT_R$. Then opamp 2810 will output $IaR_FDT_S$ where I is the current through resistors 2802, 2804, 2852, and 2854 at calibration temperature with a bias of V volts and $R_F$ is the resistance of feedback (temperature insensitive) resistors 2806 and 2856; note that the $DT_A$ terms cancel out. Similarly, opamp 2860 will output I Lastly, divider 2870 will take the ratio of is inputs and output $DT_S/DT_R$ to output buffer 2872. Thus if the irradiance of the infrared source changes by a factor, both $DT_S$ and $DT_R$ will change by the same factor and not affect the ratio output And when the concentration of a gas to be measured varies, $DT_S$ will vary while $DT_R$ remains relatively constant so the output ratio produces the desired detection signal.

Electronic chopping may be applied by use of two circuits of the FIG. 9a type to supply inputs to divider 2870. Divider 2870 may be an opamp with an analog multiplier in the feedback loop.

If the calibration resistances of resistors 2802, 2804, 2852, and 2854 are not equal, then this can be overcome by adjusting the applied bias voltages (e.g., voltage dividers) to make the calibration currents equal. Of course, all of the foregoing employed linear approximations which should suffice with the small changes in temperature expected.

Thermal compensation

Figure 29:
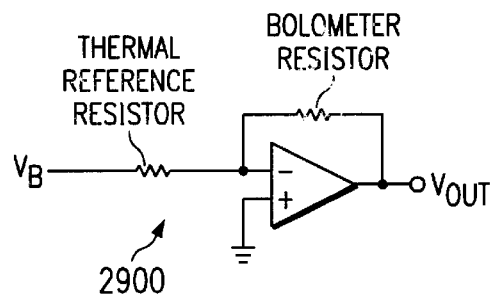
FIG. 29 is a schematic diagram of a thermal compensation preferred embodiment.

The resistivity of a bolometer resistor depends upon its temperature which, in turn, depends upon ambient temperature plus the heating due to incident radiation. Compensation for the ambient temperature changes (thermal compensation) may be approached with three kinds of reference resistors: an opaque bolometer resistor (a light shielded bolometer), a infrared light insensitive bolometer (a bolometer with the absorber removed), and a thermally sunk resistor made of bolometer resistor material (the substrate reference resistor). In each case input radiation will not affect the reference resistor, but the reference resistor will track ambient(substrate temperature. FIG. 29 shows circuit 2900 which provides thermal compensation with Vout=−$(R_B/R_R)V_B$ where $R_B$ is the resistance of the bolometer resistor and $R_R$ is the resistance of the reference resistor. Thus if the ambient temperature changes by $DT_A$, the infrared radiation heating of the bolometer resistor further changes its temperature by $DT_I$, and both resistors have a temperature coefficient of resistivity of a, then the linear approximation change of resistances due to these temperature changes amounts to multiplying $R_B$ by the factor $(1+aDT_A)(1+aDT_I)$ and multiplying $R_R$ by the factor $(1+aDT_A)$. Hence the factors $(1+aDT_A)$ and Vout changes only by the factor $(1+aDT_I)$ and reflects the input infrared radiation.

Duplicate detectors to increase sensitivity

A problem in sensing multiple gases with a sensor having multiple detectors such as sensor 1400 is the differing strengths of absorption by the various gases in their selected absorption bands. Another problem arises from different gases requiring different levels of concentration detection. For example, if both CO and CO2 were to be detected, then the greater toxicity of CO suggests the sensor should have greater sensitivity for CO than for CO2, but CO2 absorbs more strongly in a band at 4.26 microns wavelength than CO absorbs at 4.74 microns. Hence, a sensor with a bolometer detector for each gas will be more sensitive to CO2 rather than the desired converse. From a manufacturing perspective it is desirable to create as universal a sensor platform as possible so that many products can be made with the same materials. The vacuum package described in this document allows for versatility in gas sensor design as the optical filters which determine the gas to be sensed are placed on after the detector package is made. This becomes even more useful when it is possible to modify sensitivity of the system to various chemical species within the framework of the same sensor system.

Figure 30A:
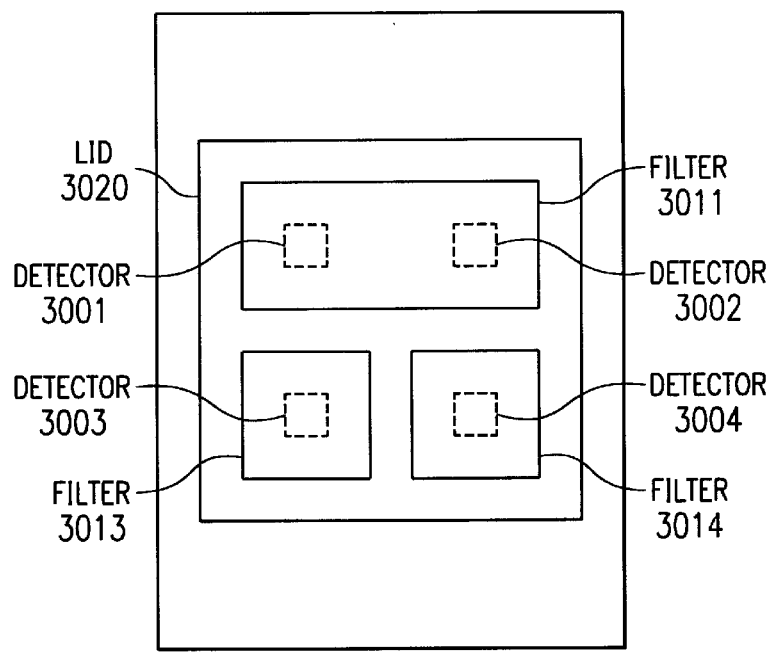
FIGS. 30a–b illustrate preferred embodiment arrays with duplicate detectors.

The preferred embodiment overcomes both problems by using simple multiple detectors for a single gas to increase sensor sensitivity for that gas. The multiple detectors may either be connected in parallel for a larger signal or treated as separate samplings of the gas and have separate circuitry. FIG. 30a shows in plan view a single vacuum package 2 by 2 array of detectors with detectors 3001 and 3002 behind single filter 3011 with a pass band at 4.74 microns wavelength to sense CO, detector 3003 behind filter 3013 with a passband at 4.26 microns to sense CO2, and detector 3004 behind filter 2914 with a passband at 3.6 microns wavelength for reference. Of course, filter 3011 could be two separate filters at the same wavelength. The 2 by 2 array would be used in a sensor analogous to sensor 1400. Multiple wavelengths could be used to sense the same species if the desired outcome was an increase in selectivity as well as an increase in sensitivity. In this way a wavelength could be chosen which had an interference band from another substance, and a second band chosen where there was no interference. The effect of the substance in question could be then retrieved from the interference band, and the signal from both bands combined. Of course the same result could be achieved by making the second band chosen as that of the interference and removing that portion of the signal from detector output.

Figure 30B:
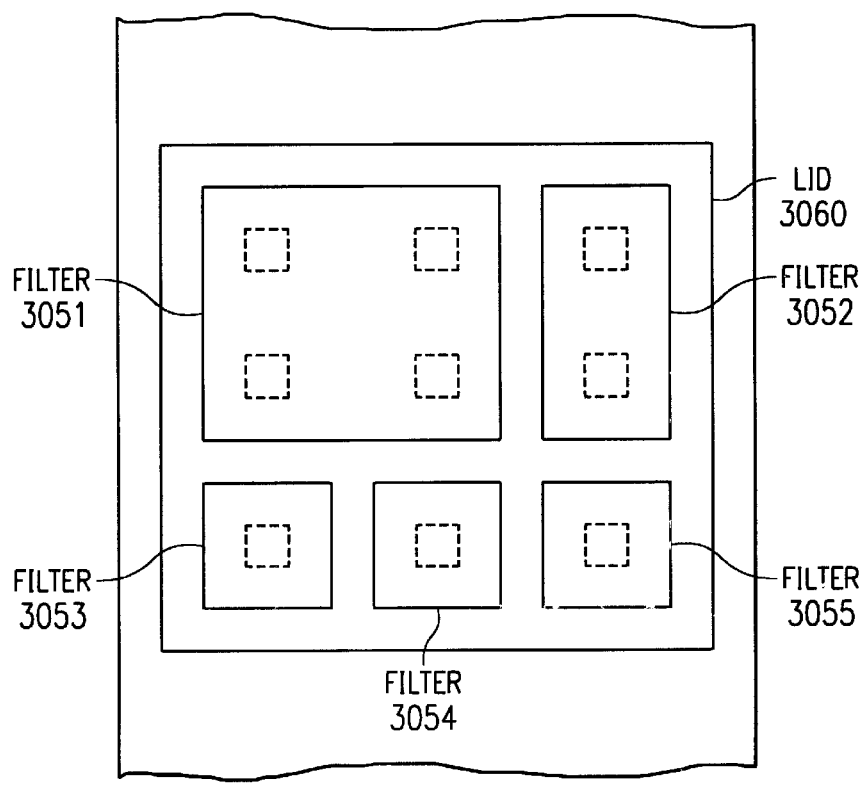

Similarly, FIG. 30b illustrates a single package 3×3 array with 4 detectors behind filter 3051 for CO, two detectors behind filter 3052 for CO2 and one detector behind each of filters 2953–2955 for each of H2O, volatile organic, and reference. Other arrays such as 2 by 3 or 1 by 4 could be used in the same manner. Taken to an extreme the spectrometer described in this document could be configured as groups of detectors under specific filters and the relative proportion of those filter being tied to the relative absorption strengths and determined after the detector package is assembled.

It is important to note that the same physical results could be obtained by preferentially increasing the sensitive area for one channel as opposed to another. This would not be as desirable as it would commit the part to more specific applications and increase costs.

Modification

The preferred embodiments may be varied in many ways while retaining one or more of the features of vacuum packaged multiple detectors, superpixels, ramped foot supports, internal shade, underlying supports for close packing, and so forth.

For example, selections of various electronic chopping arrangements, packagings, pixel structures, filter setups, and radiation sources may be made to form various sensor systems. The gasses or liquids spectrally analyzed could be selected on various criteria, the bolometer sensitivities could be varied by the size and number of pixels, The dimensions and materials may be changed provided the functional characteristics remain. The bolometer structure can include other support arrangements such as four comer posts, support arms extending towards the pixel center, a common infrared absorbing and resistance changing material, the support arms and the bolometer membrane may be made of common or separate materials, and so forth.

The electronic chopping frequency should be greater than the 1/f knee frequency, and the 1/f knee for photoconductors depends upon the bandgap (maximum wavelength detectable) and temperature. For example, mercury cadmium telluride with a bandgap of about 0.25 eV (corresponding to 5 mm wavelength), the 1/f knee at room temperature is a few Hz, so the bias switching must be at least a few Hz.

A general current source with reversible polarity with either ac of dc readout can be electronically chopped by reversing polarity as in the preferred embodiments.

What is claimed is:

1. A radiation detector, comprising:
   (a) a substrate containing circuitry;
   (b) a planar array of bolometers, each of said bolometers suspended over said substrate, each of said bolometers with resistance dependent upon temperature; and
   (c) each of said bolometers with a plurality of support arms supporting said each bolometer on said substrate, said support arms of width greater than the spacing between adjacent bolometers, said support arms including conductors connecting said bolometers to said circuitry with said bolometers connecting in parallel.

2. The radiation detector of claim 1, wherein:

(a) said bolometers are arranged in rows and columns; and (b) said support arms connect to column conductors on said substrate, said column conductors under said columns of bolometers.

3. A radiation detector, comprising:

(a) a substrate containing circuitry;

(b) a plurality of bolometers, each of said bolometers suspended over said substrate, each of said bolometers with resistance dependent upon temperature; and (c) each of said bolometers with a plurality of support arms supporting said each bolometer on said substrate, said support arms located totally between said bolometers and said substrate, spacing between adjacent pairs of said bolometers less than spacing between adjacent pairs of said support arms, and said support arms include conductors connecting said bolometers to said circuitry.

4. The radiation detector of claim 3, wherein:

(a) said bolometers are arranged in rows and columns; and (b) said support arms connect to column conductors on said substrate, said column conductors under said columns of bolometers.

5. The radiation detector of claim 4, wherein:

(a) said bolometers are coplanar and parallel to a surface of said substrate; and (b) each of said support arms has a portion extending parallel to an edge of said bolometer and is spaced from said bolometer.

6. The radiation detector of claim 3, wherein:

(a) said bolometers are arranged in rows and columns, with all of said bolometers in a column connected in parallel, and said columns connected in series.

7. An array of bolometers, comprising:

(a) an array of bolometers, each of said bolometers suspended over a substrate, each of said bolometers with resistance dependent upon temperature; and (b) each of said bolometers with a plurality of support arms supporting said each bolometer on said substrate, said support arms totally between said bolometers and said substrate, spacing between adjacent pairs of said bolometers less than spacing between adjacent pairs of said support arms.

8. The array of bolometers of claim 7, wherein:

(a) said bolometers are arranged in rows and columns; and (b) said support arms connect to column conductors on said substrate, said column conductors under said columns of bolometers.

9. The array of bolometers of claim 7, wherein:

(a) said bolometers are coplanar and parallel to a surface of said substrate; and (b) each of said support arms has a portion extending parallel to an edge of said bolometer and is spaced from said bolometer.

* * * * *

UNITED STATES PATENT AND TRADEMARK OFFICE
CERTIFICATE OF CORRECTION

PATENT NO. : 6,392,232 B1
DATED : May 21, 2002
INVENTOR(S) : Roland W. Gooch et al.

It is certified that error appears in the above-identified patent and that said Letters Patent is hereby corrected as shown below:

<u>Title page,</u>
Item [73], after Assignee:, delete "Pharmacopeia, Inc, Cranbury, NJ (US)", and insert -- Texas Instruments Incorporated, Dallas, TX (US) --.

<u>Column 5,</u>
Line 2, after "Control-", delete "ting", and insert -- timing --.
Line 21, after "polarity", insert -- ; --.

<u>Column 8,</u>
Line 9, after "$V_1$", delete "$V_2$,", and insert -- $V_2$ --.
Line 55, after "equals", delete "—V", and insert -- _V --.

<u>Column 14,</u>
Line 49, after "about 4", delete "mm", and insert -- $\mu$m --.
Line 60, after "connect the", delete "comers", and insert -- corners --.

<u>Column 15,</u>
Line 29, after "curling is", delete "minimize", and insert -- minimized --.
Line 52, after "such as", delete "50 m", and insert -- 50$\mu$m by 50$\mu$m --.

<u>Column 17,</u>
Line 7, after "needs to be", delete "upended", and insert -- suspended --.

<u>Column 18,</u>
Line 14, after "resistor", delete "terminal", and insert -- terminals --.
Line 41, after "24a", delete ",".
Line 43, after "2412", delete ";".

<u>Column 21,</u>
Line 12, after "10.0 to 20.0", insert -- $\mu$m --.

<u>Column 22,</u>
Line 53, after "output", delete "I", and insert -- $IaR_FDT_R$ --.

<u>Column 23,</u>
Line 16, after "ambient", delete "(", and insert -- / --.
Line 62, after "filter", delete "2914", and insert -- 3014 --.

UNITED STATES PATENT AND TRADEMARK OFFICE
CERTIFICATE OF CORRECTION

PATENT NO.    : 6,392,232 B1
DATED         : May 21, 2002
INVENTOR(S)   : Roland W. Gooch et al.

It is certified that error appears in the above-identified patent and that said Letters Patent is hereby corrected as shown below:

<u>Column 24,</u>
Line 13, after "filters", delete "2953-2955", and insert -- 3052-3055 --.
Line 25, delete "Modification" and insert -- Modifications --.
Line 40, delete "comer" and insert -- corner --.

Signed and Sealed this

Nineteenth Day of November, 2002

*Attest:*

*Attesting Officer*

JAMES E. ROGAN
*Director of the United States Patent and Trademark Office*